US011633441B2

(12) United States Patent
Sutter et al.

(10) Patent No.: US 11,633,441 B2
(45) Date of Patent: Apr. 25, 2023

(54) IMMUNO-MODULATED REPLICATION-EFFICIENT VACCINIA VIRUS STRAIN

(71) Applicants: Gerd Sutter, Munich (DE); Juan José Rojas Exposito, Munich (DE)

(72) Inventors: Gerd Sutter, Munich (DE); Juan José Rojas Exposito, Munich (DE)

(73) Assignees: Sutter Gerd, Munich (DE); Rojas Exposito Juan José, Munich (DE)

( * ) Notice: Subject to any disclaimer, the term of this patent is extended or adjusted under 35 U.S.C. 154(b) by 376 days.

(21) Appl. No.: 16/768,489

(22) PCT Filed: Dec. 3, 2018

(86) PCT No.: PCT/EP2018/083318
§ 371 (c)(1),
(2) Date: May 29, 2020

(87) PCT Pub. No.: WO2019/106205
PCT Pub. Date: Jun. 6, 2019

(65) Prior Publication Data
US 2020/0376051 A1    Dec. 3, 2020

(30) Foreign Application Priority Data
Dec. 1, 2017 (DE) .................... 10 2017 128 538.5

(51) Int. Cl.
*A61K 35/768*     (2015.01)
*A61K 39/00*      (2006.01)
*C12N 7/00*       (2006.01)

(52) U.S. Cl.
CPC ........ *A61K 35/768* (2013.01); *A61K 39/0011* (2013.01); *C12N 7/00* (2013.01); *A61K 2039/585* (2013.01); *C12N 2710/24121* (2013.01); *C12N 2710/24132* (2013.01); *C12N 2710/24134* (2013.01)

(58) Field of Classification Search
CPC .......... A61K 39/285; A61K 2039/5252; A61K 2039/53
See application file for complete search history.

(56) References Cited

U.S. PATENT DOCUMENTS

| 2003/0198623 A1 | 10/2003 | Paoletti et al. |
| 2006/0275777 A1 | 12/2006 | Waelti |
| 2016/0129135 A1 | 5/2016 | Kirn |

FOREIGN PATENT DOCUMENTS

| EP | 2136633 | 9/2008 |
| EP | 2529010 B1 | 4/2017 |
| JP | 1994-503227 A | 4/1994 |
| JP | 2006-506974 A | 3/2006 |
| JP | 2016-506722 A | 3/2016 |
| WO | WO-2004/014314 A2 | 2/2004 |
| WO | WO-2005/017208 A1 | 2/2005 |

OTHER PUBLICATIONS

Written Opinion for International Patent Application No. PCT/EP2018/083318, dated Nov. 26, 2019 (11 pages).
International Preliminary Report on Patentability for International Patent Application No. PCT/EP2018/083318, dated Mar. 6, 2020 (12 pages).
International Search Report for International Patent Application No. PCT/EP2018/083318, dated Mar. 25, 2019 (21 pages).
Goebel et al., "The complete DNA sequence of vaccinia virus," Virology. 179(1): 247-266 (1990).
Drexler et al., "Highly attenuated modified vaccinia virus Ankara replicates in baby hamster kidney cells, a potential host for virus propagation, but not in various human transformed and primary cells," J Gen Virol. 79(2) 347-352 (1998).
Chang et al., "Vaccinia virus A25 and A26 proteins are fusion suppressors for mature virions and determine strain-specific virus entry pathways into HeLa, CHO-K1, and L cells," J Virol. 84(17):8422-8432 (2010).
DeHaven et al., "The vaccinia virus A56 protein: a multifuncional transmembrane glycoprotein that anchors two secreted viral proteins," J Gen Virol. 92(9):1971-1980 (2011).
Tartaglia et al., "NYVAC: a highly attenuated strain of vaccinia virus," Virol. 188:217-232 (1992).

*Primary Examiner* — Bao Q Li
(74) *Attorney, Agent, or Firm* — Clark & Elbing LLP

(57) ABSTRACT

The invention refers to new immuno-modulated replication-efficient Vaccinia virus strain (IOVA) and its derivatives for the use in medicine.

14 Claims, 18 Drawing Sheets
Specification includes a Sequence Listing.

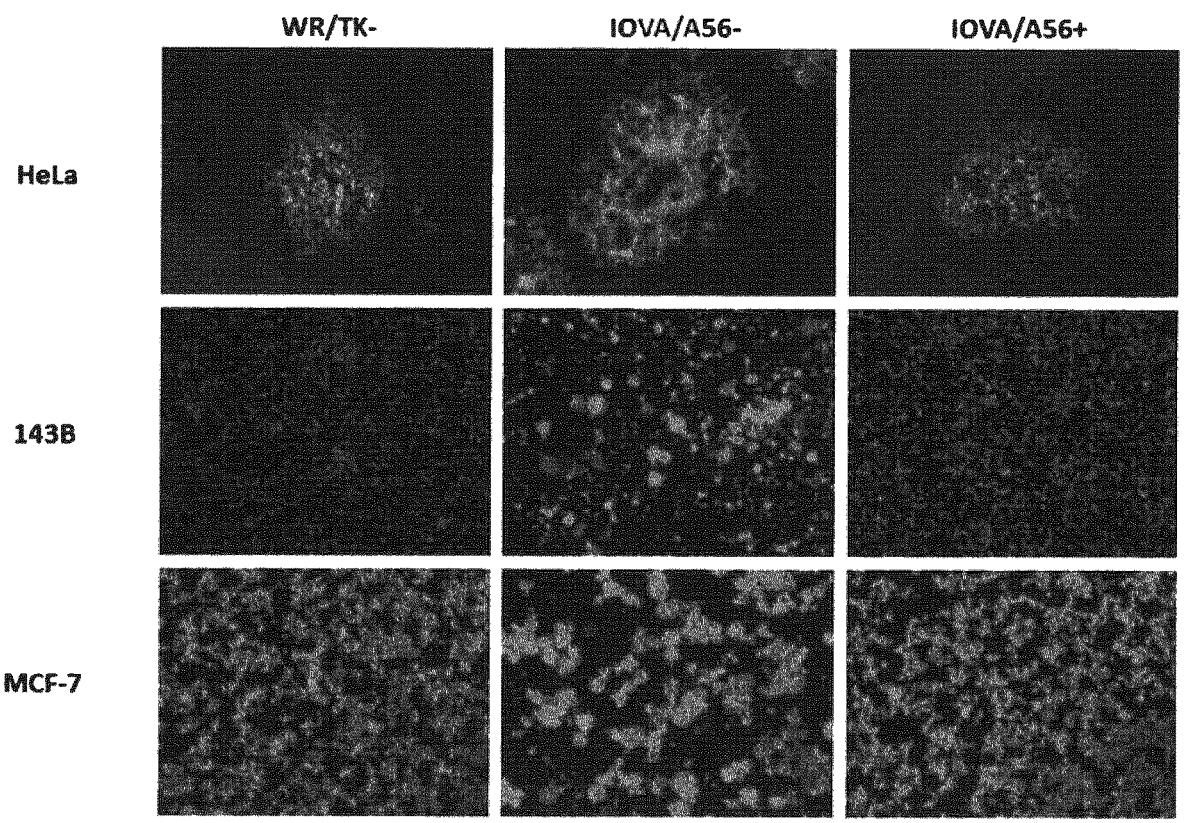
Fig.: 1a

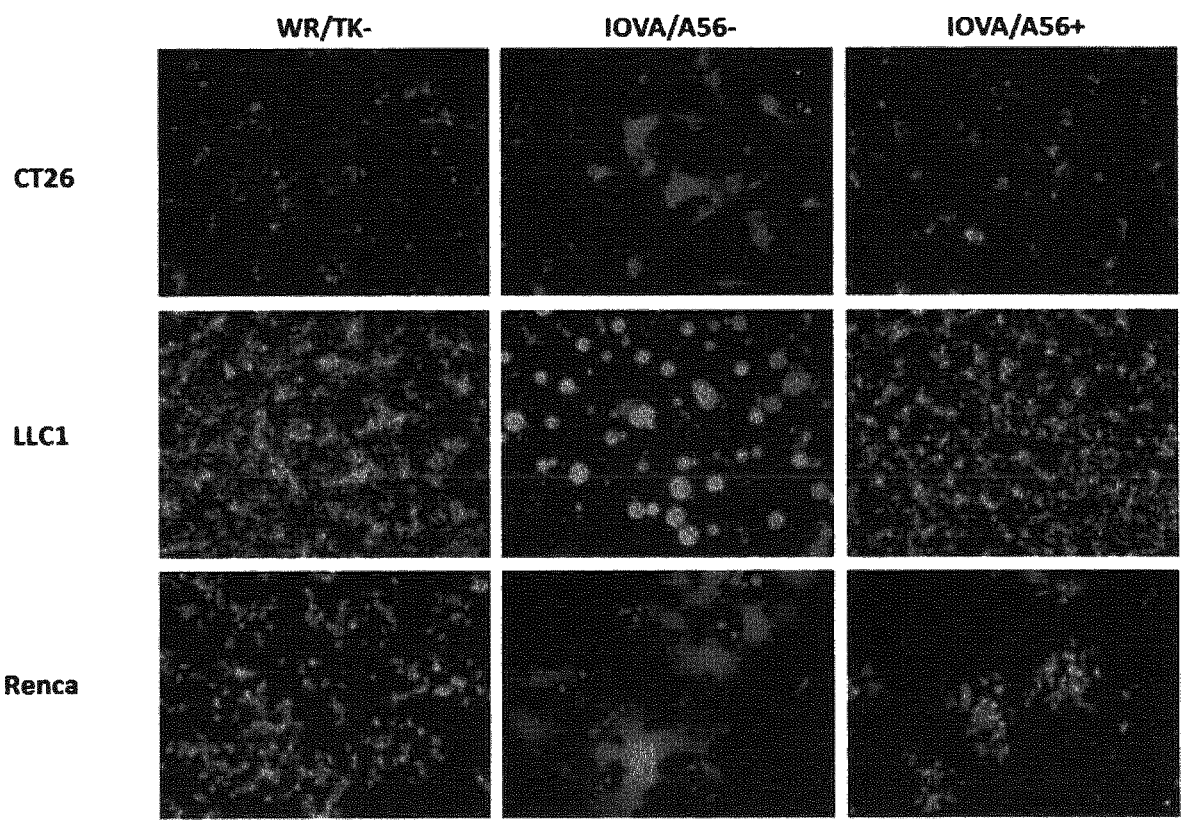
Fig.: 1b

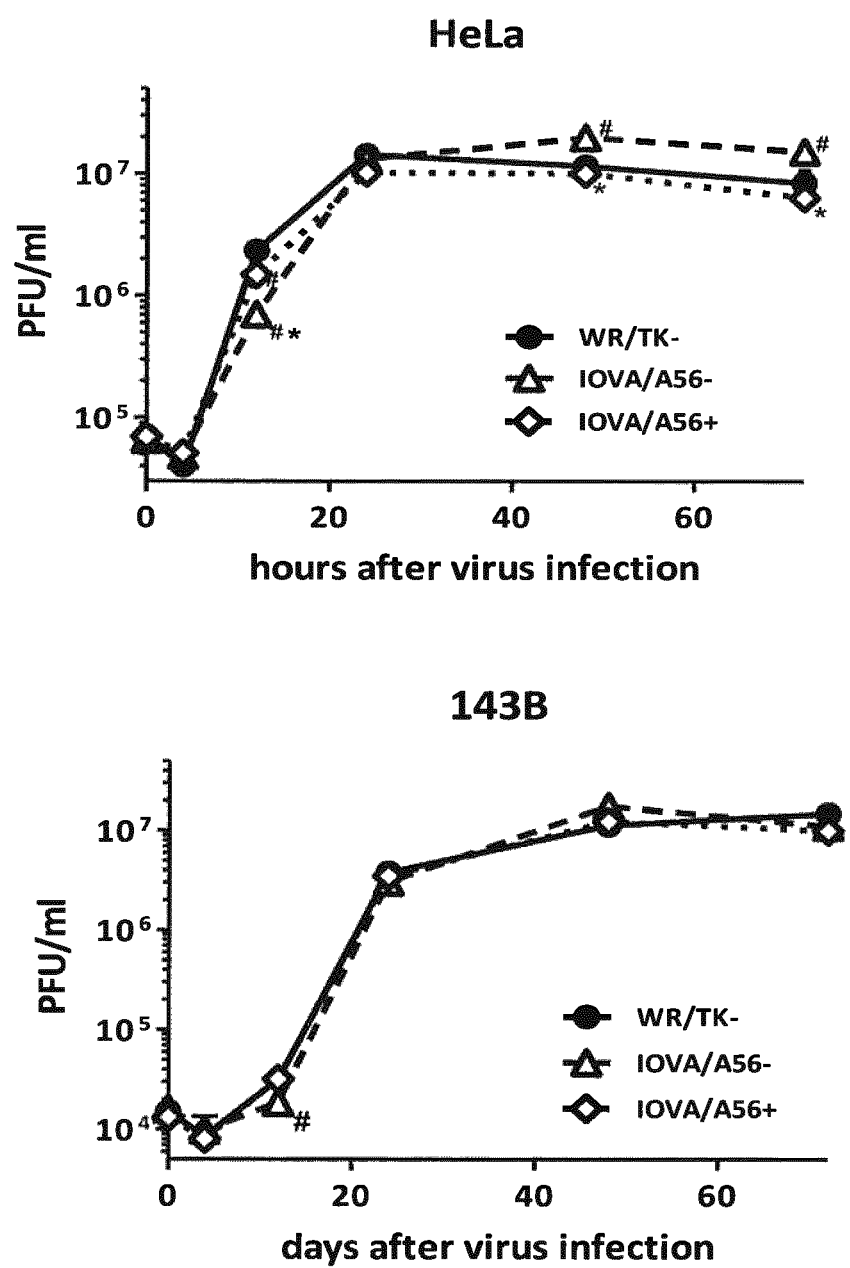
Fig.: 2a

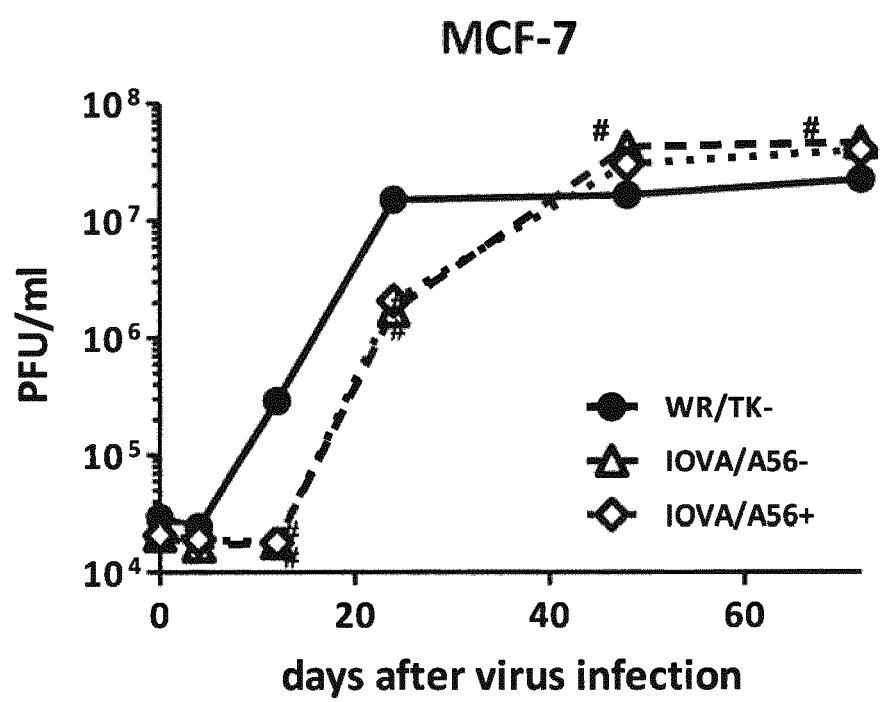
Fig.: 2a continuing

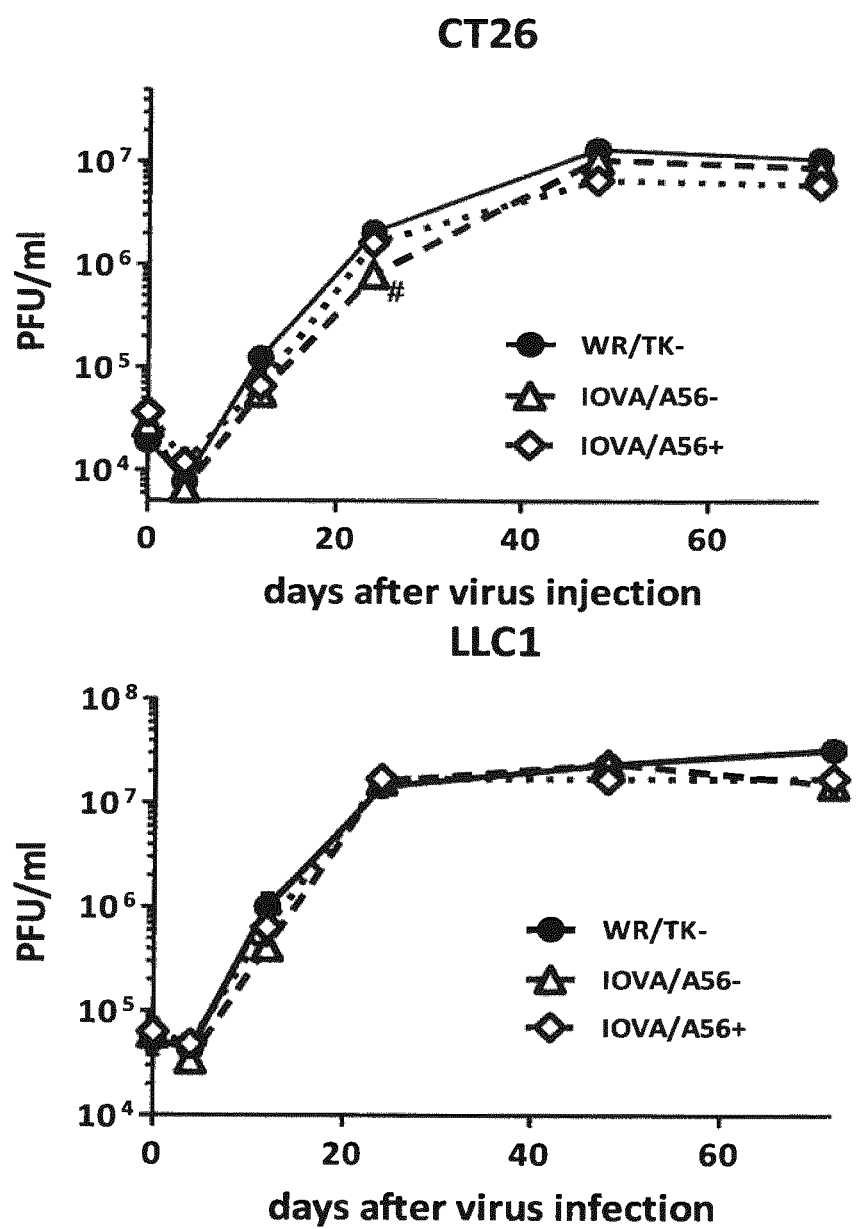
Fig.: 2b

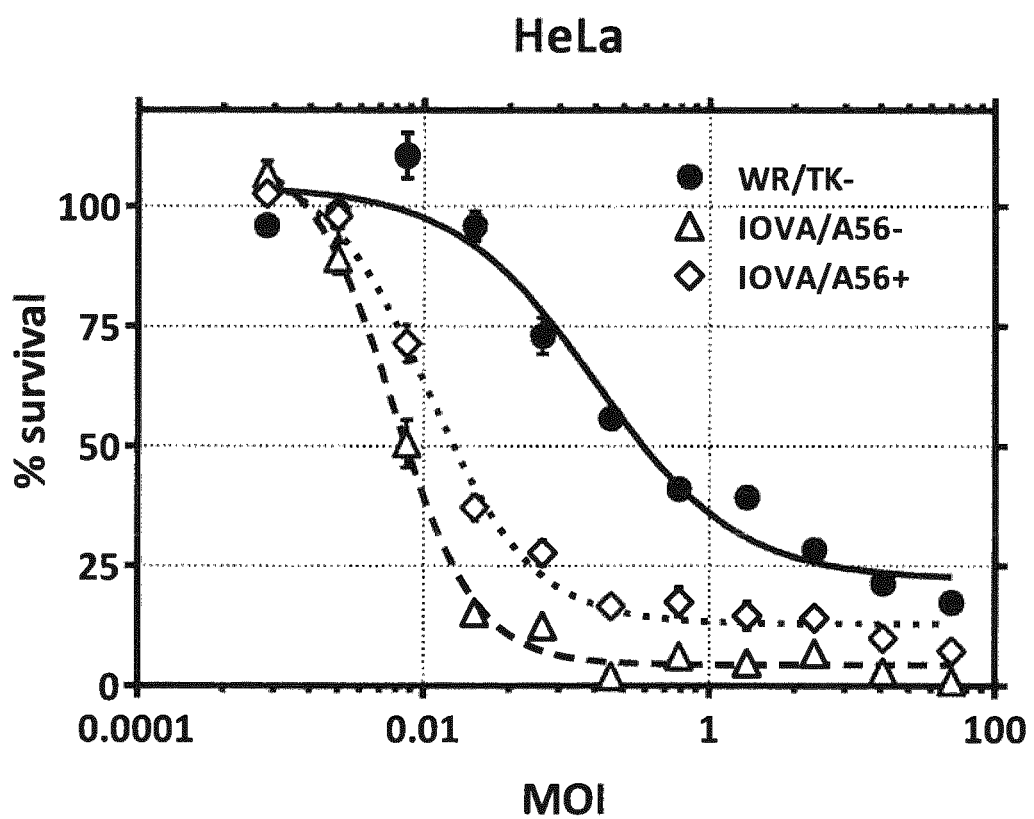
Fig.: 3a

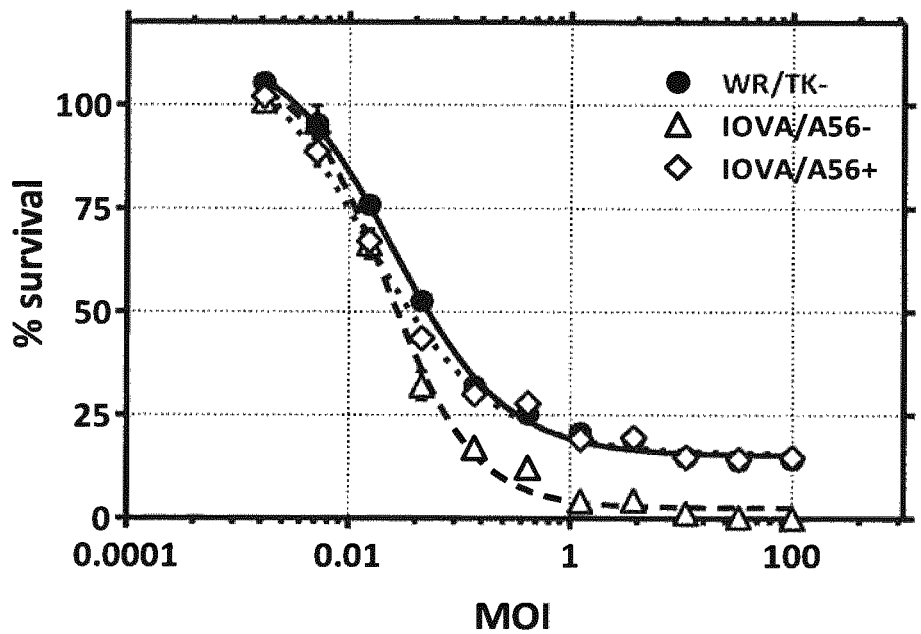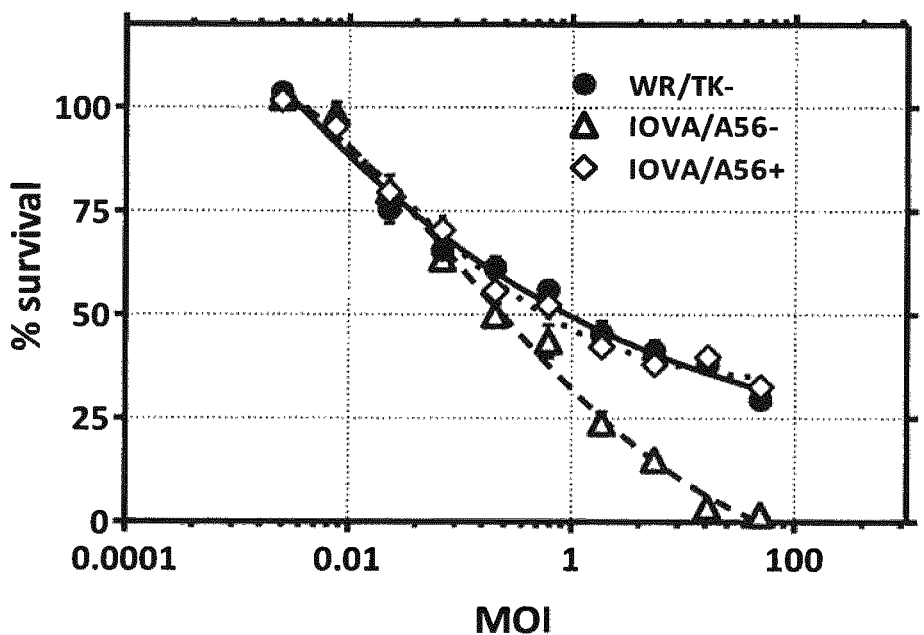
Fig.: 3a continuing

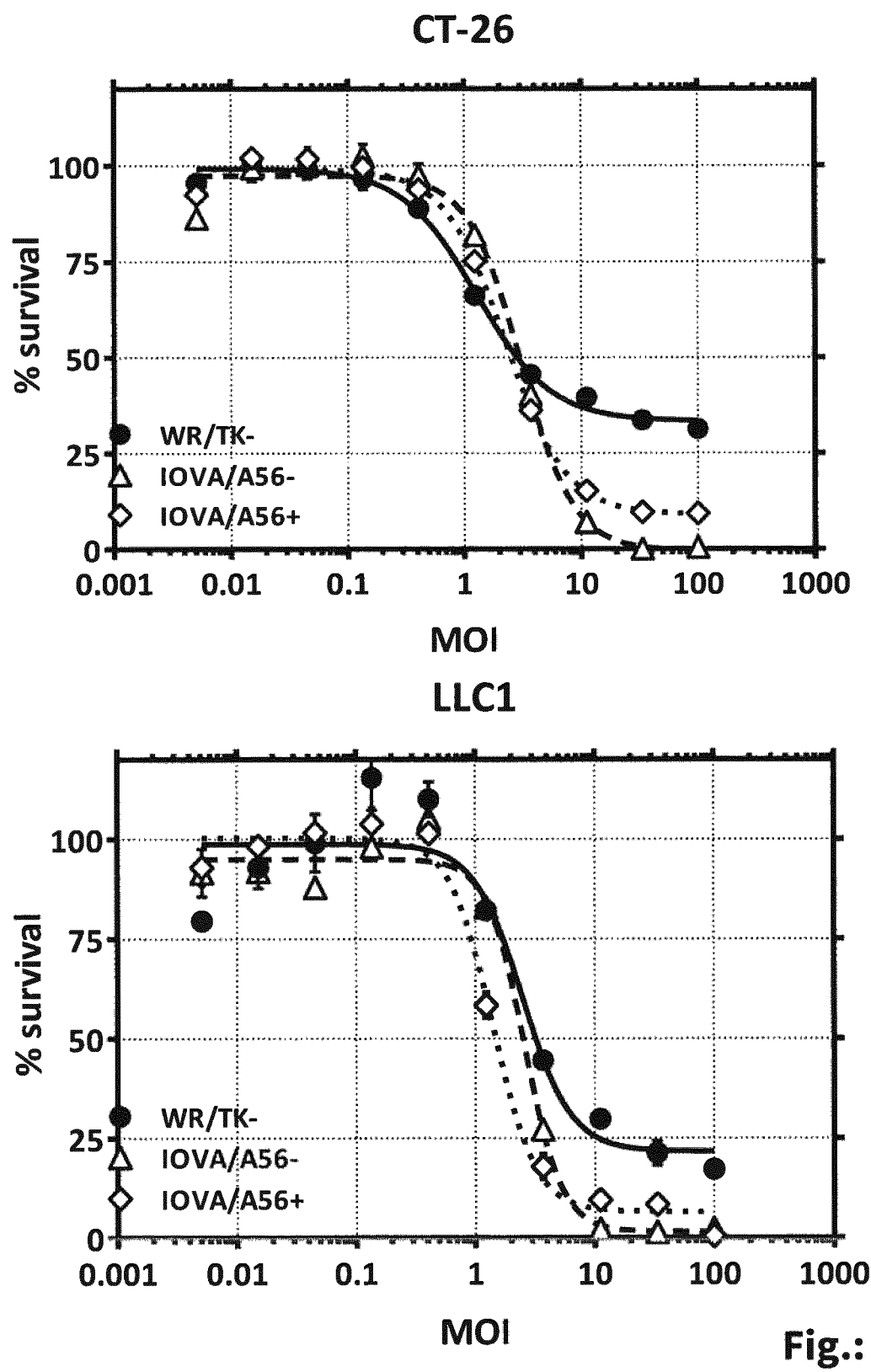
Fig.: 3b

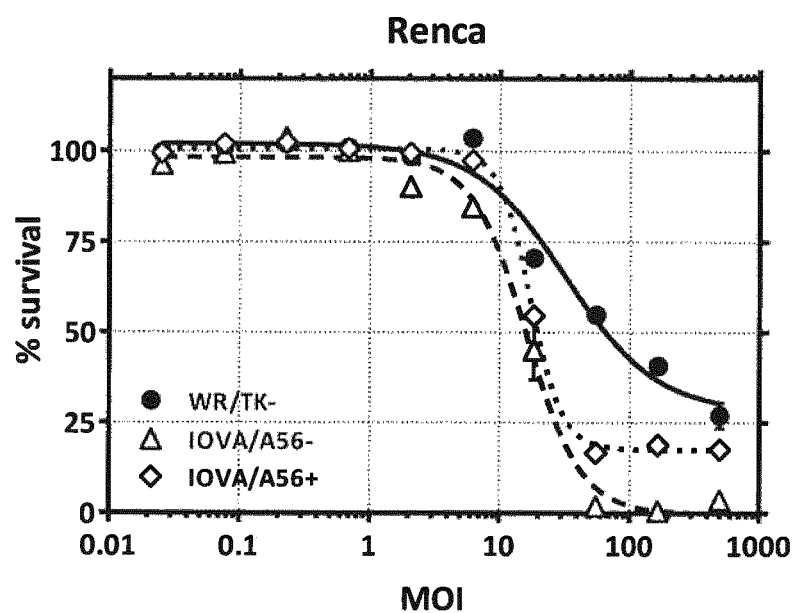
Fig.: 3b continuing

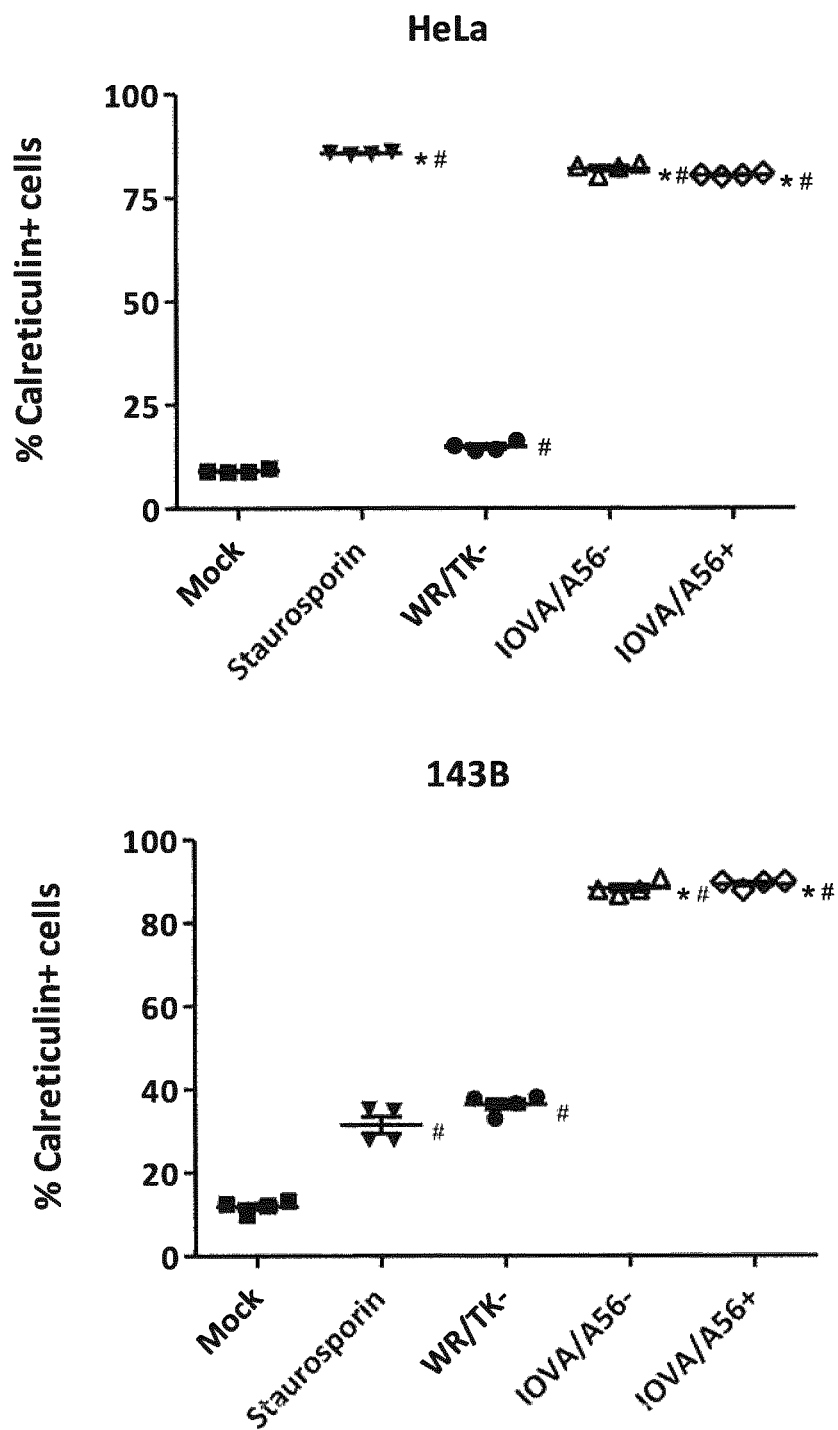
Fig.: 4a

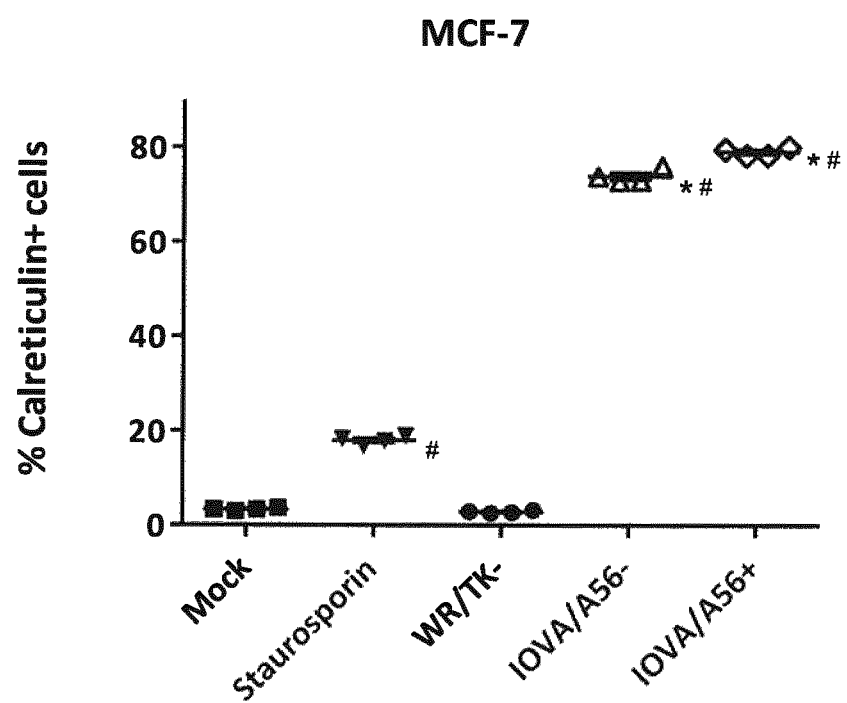
Fig.: 4a continuing

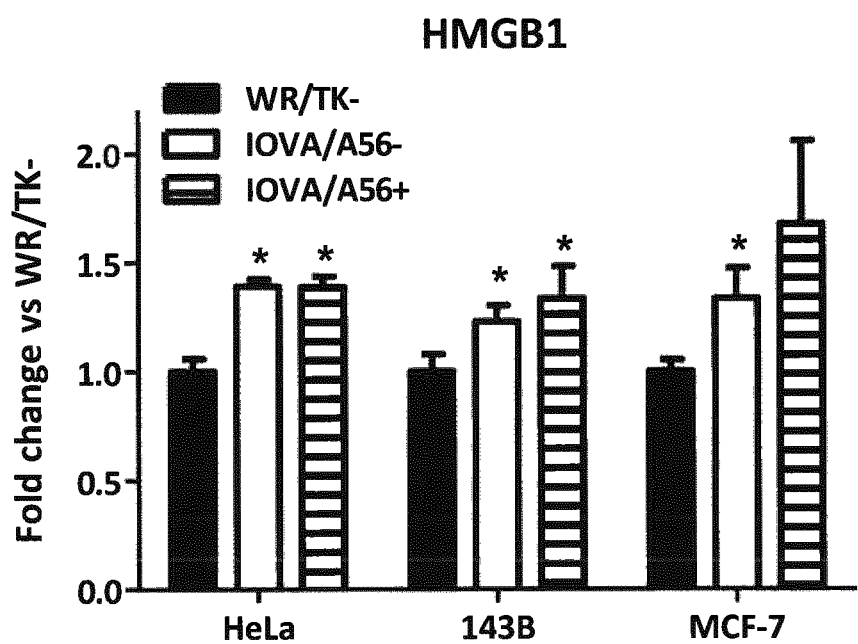
Fig.: 4b

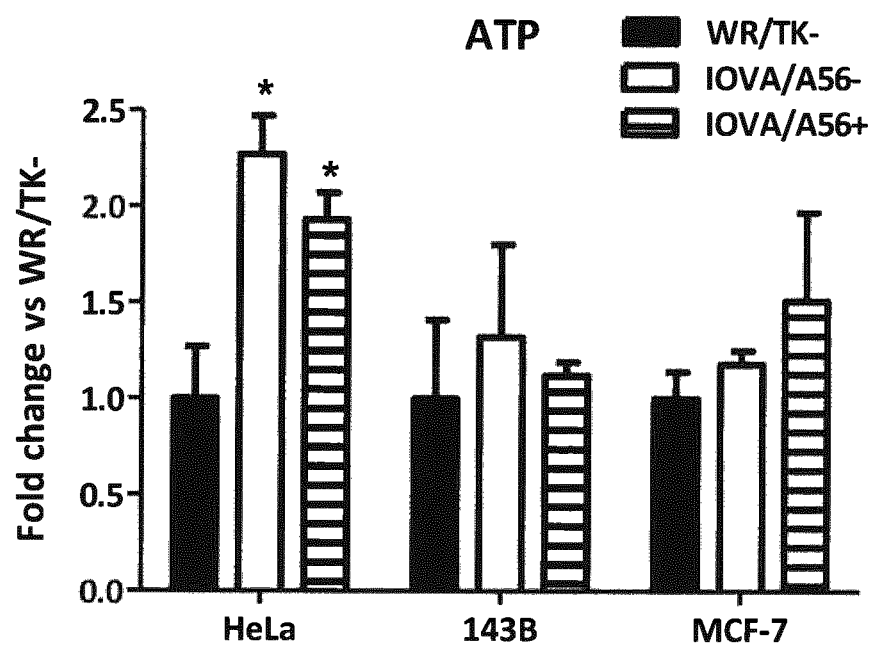
Fig.: 4c

```
CTATTGTAGAAATTGTTTTTCACAGTTGCTCAAAAACGATGGCAGTGACTTATGAGTTTCATCTTT
AGTAAACATATCATAATATTCGATATTACTAGTTGACATATCGAACAAATTCCAAGTATTTGATTT
TGGATAATATTCGTATTTTGCATCTGCTATAATTAAGATATAATCACCGCAAGAACACACGAACAT
CTTTCCTACATGGTTAAAGTACATGTACAATTCTATCCATTTGTCTTCCTTAACTATATATTTGTA
TAGATAATTACGAGTCTCGTGAGTAATTCCAGTAATTACATAGATGTCGCCGTCGTACTCTACAGC
ATAAACTATACTATGATGTCTAGGCATGGGAGACTTTTTTATCCAACGATTTTTAGTGAAACATTC
CACATCGTTTAATACTACATATTTTTCATCGTGGTATAAACTCCACCCATTACATATATATCATC
GTTTACGAATACCGACGCGCCTGAATATCTAGGAGTAATTAAGTTTGGAAGTCTTATCCATTTCGA
AGTGCCGTGTTTCAAATATTCTGCCACACCCGTTGAAATAGAAAATTCTAATCCTCCTATTACATA
TAACTTTCCATCGTTAACACAAGTACTAACTTCTGATTTTAACGACGACATATTAGTAACCGTTTT
CCATTTTTTCGTTTCAAGATCTACCCGCGATACGGAATAAACATGTCTATTGTTAATCATGCCGCC
AATAATGTATAGACAATTATGTAAACATTTGCATTATAGAATTGTCTATCTGTATTACCGACTAT
CGTCCAATATTCTGTTCTAGGAGAGTAATGGGTTATTGTGGATATATAATCAGAGTTTTAATGAC
TACTATATTATGTTTTATACCATTTCGTGTCACTGGCTTTGTAGATTTGGATATAGTTAATCCCAA
CAATGATATAGCATTGCGCATAGTATTAGTCATAAACTTGGGATGTAAAATGTTGATGATATCTAC
ATCGTTTGGATTTTTATGTATCCACTTTAATAATATCATAGCTGTAACATCCTCATGATTTACGTT
AACGTCTTCGTGGGATAAGATAGTTGTCAGTTCATCCTTTGATAATTTTCCAAATTCTGGATCGGA
TGTCACCGCAGTAATATTGTTGATTATTTCTGACATCGACGCATTATATAGTTTTTTAATTCCATA
TCTTTTAGAAAAGTTAAACATCCTTATACAATTTGTGGAATTAATATTATGAATCATAGTTTTTAC
ACATAGATCTACTACAGGCGGAACATCAATTATTATGGCAGCAACTAGTATCATTTCTACATTGTT
TATGGTGATGTTTATCTTCTTCCAGCGCATATAGTCTAATAGCGATTCAAACGCGTGATAGTTTAT
ACCATTCAATATAATCGCTTCATCCTTTAGATGGTGATCCTGAATGCGTTTAAAAAAATTATACGG
AGACGCCGTAATAATTTCCTTATTCACTTGTATAATTTCCCCATTGATAGAAAATATCACGCTTTC
CATTCTTGAAGTACTATAAGTAATTATAGTATAATGTAAAGGTTTATATATTCAATATTTTTATA
AAAAAATCATTTCGACATTAATTCCTTTTTAAATTTCCGTCTATCATCTATAGAAACATATTCTAT
GAATTTATAAAATGCTTTTACGTGTCCTATCGTAGGCGATAGAACCGCTAAAAGCCTATCGAATT
TCTACAAAAGAATCTGTTATATGGTATAGGGAGAGTATAAAACATTAAATGTCCGTACTTATTAAA
GTATTCAGTAGCCAATCCTAACTCTTTCGAATACTTATTAATGGCTCTTGTTCTGTACGAATCTAT
TTTTTTGAACAATGGACCTAGTGGTATATCTTGTTCTATGTATCTAAAATAATGTCTGACTAGATC
CGTTAGTTTAATATCCGCAGTCATCTTGTCTAGAATGGCAAATCTAACTGCGGGTTTAGGCTTTAG
TTTAGTTTCTATATCTACATCTATGTCTTTATCTAACACCAAAAATATAATAGCTAATATTTTATT
ACAATCATCCGGATATTCTTCTACGATCTCACTAACTAATGTTTCTTTGGTTATACTAGTATAGTC
ACGATCAGACAAATAAAGAAAATCAGATGATCGATGAATAATACATTTAAATTCATCATCTGTAAG
ATTTTTGAGATGTCTCATTAAAATATTATTAGGGTCAGTACTCATTATCATTAGGCAGCTATTACT
TATTTTATTATTTTTCACCATATAGATCAATCATTAGATCATCAAAATATGTTTCAATCATCCAAG
AGTATGGTGAATGACTCTTCCCATCTAATTTCTGAACGTTCACCAATGTCTCTAGCCACTTTGGCA
CTAATAGCGATCATTCGCTTAGCGTCTTCTATATTATTAACTGGTTGATTCAATCTATCTAGCAAT
GGACCGTCGGACAGCGTCATTCTCATGTTCTTAATCAATGTACATACATCGCCGTCATCTACCAAT
TCATCCAACAACATAAGCTTTTTAAAATCATCATTATAATAGGTTTGATCGTTGTCATTTCTCCAA
```

SEQ ID No.: 1

Fig.: 5a

```
AGAATATATCTAATAAGTAGAGTCCTCATGATTAGTTAACAACTATTTTTTATGTTAAATCAATTAGTACA
CCGCTATGTTTAATACTTATTCATATTTTAGTTTTTAGGATTGAGAATCAATACAAAAATTAATGCATCAT
TAATTTTAGAAATACTTAGTTTCCACGTAGTCAATGAAACATTTGAACTCATCGTACAGGACGTTCTCGTA
CAGGACGTAACTATAAACCGGTTTATATTTGTTCAAGATAGATACAAATCCGATAACTTTTTTTACGAATT
CTACGGGATCCACTTTAAAAGTGTCATACCGGGTTCTTTTTATTTTTTAAACAGATTAATGGTGTGATGT
TGATTAGGTCTTTTACGAATTTGATATAGAATAGCGTTTACATATTCTCCATAATGGTCAATCGCCATTTG
TTCGTATGTCATAAATTCTTTAATTATATGACACTGTGTATTATTTAGTTCATCCTTGTTCATCATTAGGA
ATCTATCCAATATGGCAATTATACTAGAACTATAGGTGCGTTGTATACACATATTGATGTGTCTGTTTATA
CAATCCATGCTACTACCTTCGGGTAAAATTGTAGCATCATATACCATTTCTAGTACTTTAGGTTCATTGTT
ATCCATTGCAGAGGACGTCAT
```

SEQID No.: 1 continued

Fig.: 5a continuing

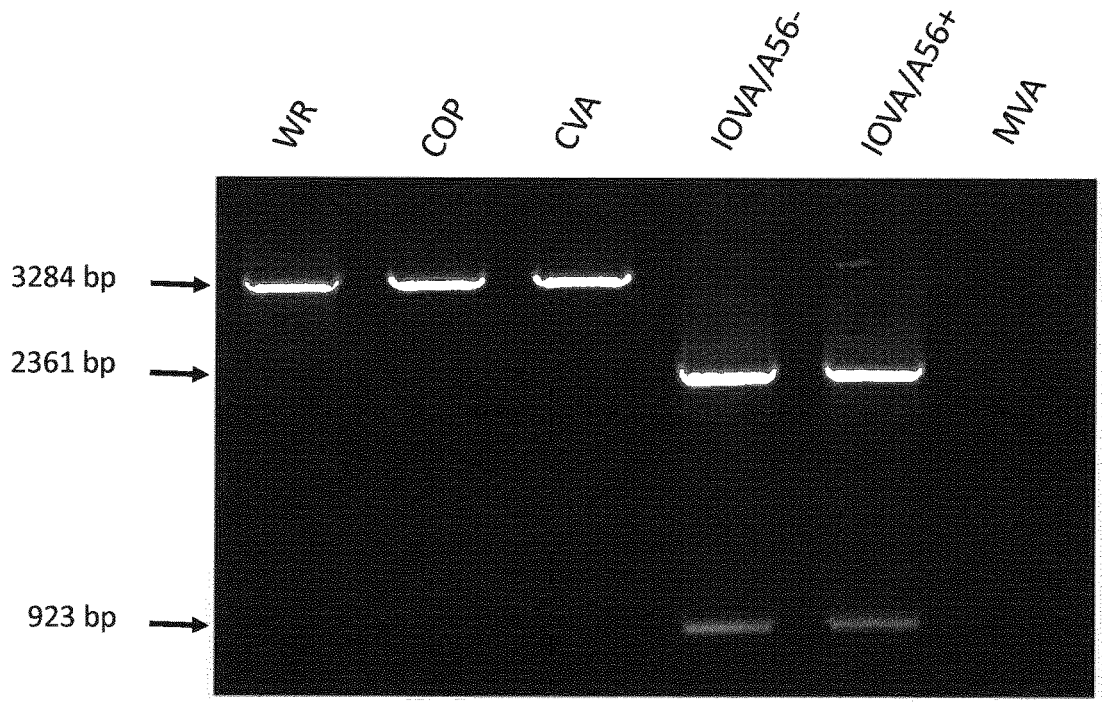

Fig.: 5b

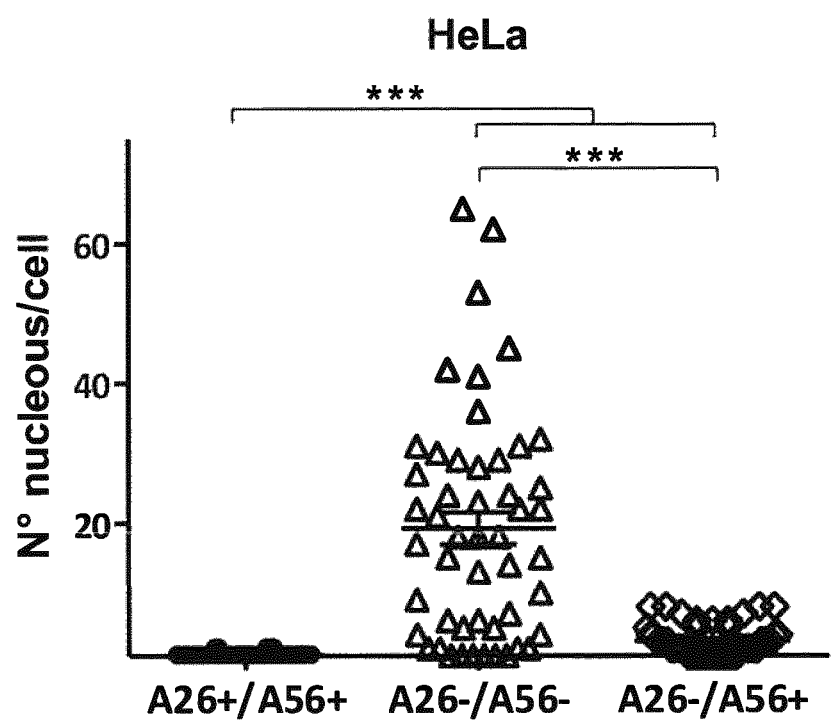
Fig.: 6

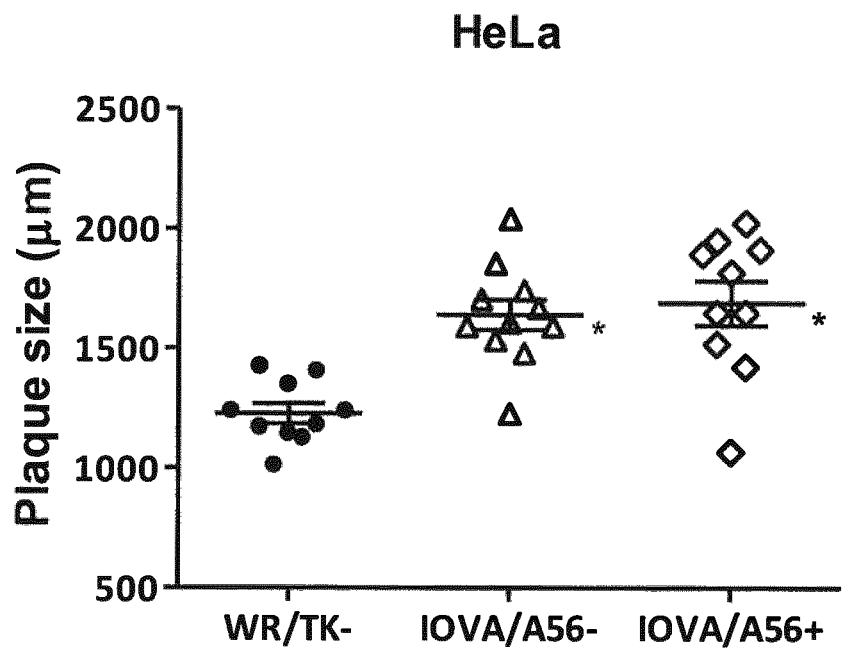
Fig.: 7a
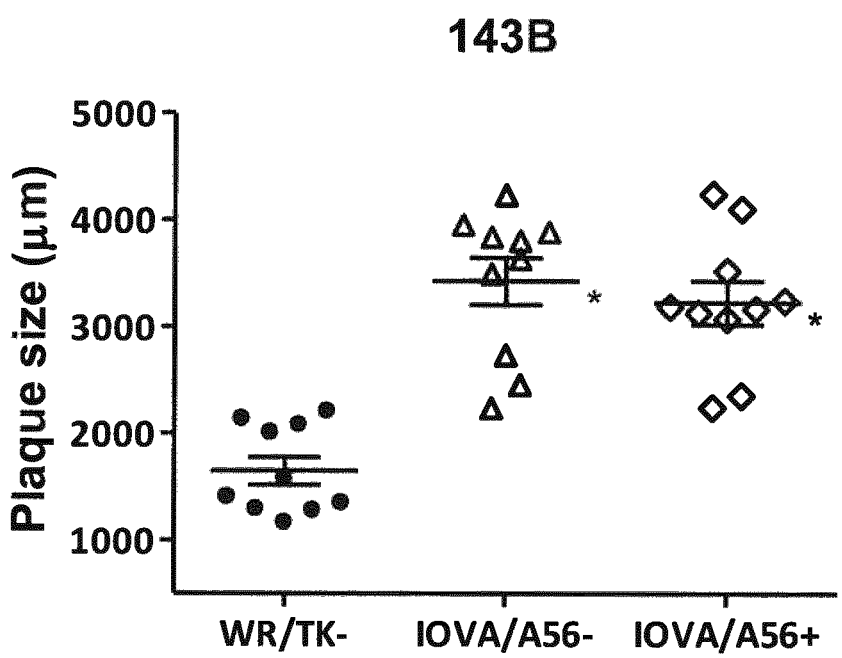
Fig.: 7b

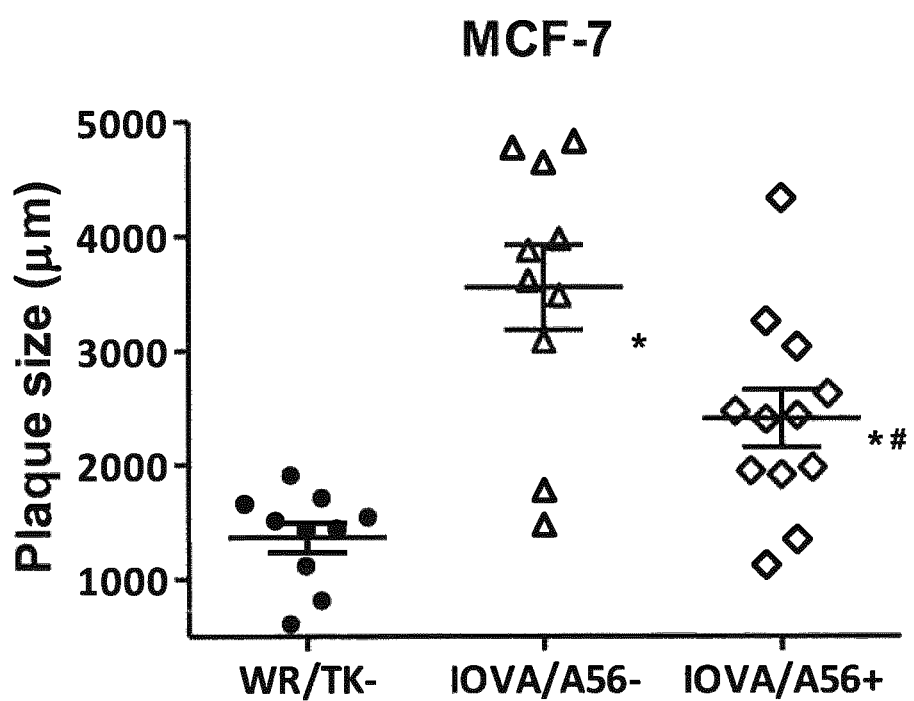
Fig.: 7c

IMMUNO-MODULATED REPLICATION-EFFICIENT VACCINIA VIRUS STRAIN

SEQUENCE LISTING

The instant application contains a Sequence Listing which has been submitted electronically in ASCII format and is hereby incorporated by reference in its entirety. Said ASCII copy, created May 28, 2020, is named 50322-004001_Sequence_Listing_05.28.20 ST25 and is 9,277 bytes in size.

FIELD OF THE INVENTION

The invention refers to new immuno-modulated replication-efficient Vaccinia virus strain (IOVA) and its derivatives for the use in medicine.

BACKGROUND OF THE INVENTION

Recently, for the first time a virus has obtained market approval to be used as an oncolytic virus in the treatment of human cancer. Such a success refocused the scientific interest on viruses in general and also on the use of Vaccinia virus for the treatment of cancer. The use of Vaccinia viruses proved already to be effective not only in vaccination approaches, e.g. protecting against poxvirus infections in man, but have also been applied in many other medical treatments and clinical trials for e.g. tumour vaccination.

The scientific community knows, from data obtained in the first clinical studies with oncolytic viruses that these viruses or designed viral vectors are capable to selectively replicate in cancer cells and actively promote the lysis of such infected cancer cells. However, the direct lysis of such infected cancer cells is rarely sufficient to eradicate bulky tumours and rarely cures metastatic disease. These results illustrate the increasing need not only for more potent and selective viruses, but also for alternative mechanisms of tumour destruction in order to avoid recurrence of the disease.

More recently, viruses and viral vectors based on Vaccinia virus were tested as oncolytics and seem to be most promising due to their capacity to destroy tumours through mechanisms different from the direct lysis of the tumour cell (Kirn et al., 2009). On the one hand it was demonstrated that the replication of the virus in tumour-associated endothelial cells leads to disruption of tumour blood flow, hypoxia, and massive tumour necrosis (Breitbach et al. 2013); on the other hand the replication of Vaccinia virus within the tumour is capable of inducing an anti-tumour immune response thanks to the release of tumour-associated antigens (TAAs) after lysis, and to an overcoming of the local immunosuppression existing within the tumour (Thorne et al., 2010).

These alternative mechanisms proved to be key in clinical evaluations, and highlighted the critical role that the immune system plays in determining the activity of oncolytic vectors. In randomized clinical trials, the most effective viruses proved to be those that express an immuno-activating cytokine in order to optimize the activation of the cellular immune response (Breitbach et al., 2011; Heo et al., 2013). However, even with these more potent cytokine-expressing viruses, some patients do not elicit an effective immune response against the tumour. Generation of effective anti-tumour immune responses require activation and collaboration of even more and different lineages of immune cells, and the expression of a single cytokine can hardly change the overall immunity elicited by a virus. Thus, research on the generation of novel strains with a higher capacity to activate a robust immune response is still needed.

It is therefore an objective of the present invention to provide newly adapted and/or more potent viruses and/or viral vectors useful for the treatment of human diseases, wherein the viruses or vectors upon infection elicit and/or activate additional and more powerful, but—for safety reasons—highly specific immune responses in the patient needing such treatment.

This object has been solved by the newly identified immuno-modulated replication-efficient Vaccinia virus strain as specified in claim 1 of the present application. Further embodiments refer to variations of this newly identified and/or adapted immuno-modulated Vaccinia virus as well as vectors, preferred uses and compositions comprising the newly identified and/or adapted Vaccinia virus strains are described in the dependent claims.

While studying the immune response to the known Vaccinia virus strains, and particularly in comparison to a well-characterised Vaccinia virus strain (Western Reserve (WR)) the inventors were able to isolate, generate and characterise a new Vaccinia virus strain. This novel strain shows a clearly improved immunological profile. Without being bound by the theory, we believe that the novel strain also shows a strong promotion of an increased immunogenic cell death upon infection of tumour cells and thereby redirects the immune reaction towards the infected and the not-yet-infected tumour cells.

The strain Vaccinia virus WR is a well-defined virus strain that has been tested as oncolytic due to its high replication capacity in tumour cells and was used for the delivery of GM-CSF for increasing the immune response against tumours. In order to provide vectors with tumour selectivity, different Vaccinia virus genes involved in activating the metabolism of infected cells were successfully deleted, restricting the replication of the resulting virus vectors to cells with a high-replication index. Deletions of genes such as thymidine kinase or viral growth factor have already been included in viral candidates tested in clinical trials (Zeh et al., 2015).

WO2015027163 is one example wherein an oncolytic Vaccinia virus is described, which comprises genomic deletions in some of the typical viral immune evasion genes. In this particular case the oncolytic virus comprises deletions in e.g. the B8R, B18R and A35R genes.

EP2136633 is another example, which describes the therapeutic use of a GM-CSF-expressing Vaccinia virus in oncolytic treatment approaches.

In these oncological approaches, Vaccinia virus WR strain is considered the current gold standard for the development and for comparison of newly developed oncolytic Vaccinia viruses.

However, beside this alleged success there are still some concerns considering Vaccinia virus WR as the basis for a therapeutic approach in severely sick cancer patients. As Vaccinia virus WR was selected in vivo after multiple passages in mouse brains, which factually resulted in a virus with high replicative capacity in mouse cells, but also in an alarming virulence due to neurotropism and neurotoxicity, which may hinder its safe use in the treatment of cancer patients.

Nevertheless, in the context of this application Vaccinia virus WR was chosen as comparison to the newly developed Vaccinia virus strain of the present invention, wherein the main goal of the present invention is to provide a novel immuno-modulated replication-competent Vaccinia virus strain with a substantially improved immunological profile and high lytic and/or oncolytic capability.

An additional comparison with the highly attenuated MVA (Modified Vaccinia Ankara) strain of Vaccinia virus seems not to be useful, as MVA is characterised by its host rang restriction or in other words its defective replication in cells from mammalian hosts. MVA has been broadly used for delivering antigens for vaccination against pathogens (for review see Volz & Sutter, 2017) and has been characterised regarding its biological and immunological profile (Meyer et al., 1991). Additionally, MVA is a highly modified Vaccinia virus unable to replicate in mammalian cells and has been previously used for vaccination against tumours by delivering tumour-associated antigens (TAA) (Zhang et al., 2012). Regardless of the fact that this virus seemed to show an ideal safety profile and was demonstrated to be effective generating an immune response against the expressed tumour antigens in vivo, most patients did not show any verifiable anti-tumour response; it seems that the elicited immunity is hindered by the immune suppression that occurs locally within the tumour, leading to an ineffective anti-tumour response (Marigo et al., 2008).

Thus, although progress could have been stated towards an improved immunotherapy, there is still need for more effective Vaccinia virus strains to be used in virotherapy of cancer in order to establish an effective immune response capable of eradicating cancers.

The present invention describes now a further step towards this goal and discloses a novel Vaccinia virus strain, which is replication competent in human and mouse cells and is—according to the best knowledge of the inventors—even the first Vaccinia virus in general that causes an immunologically relevant calreticulin (CRT) translocation to the outer membrane and thus causes an exposure of calreticulin on the outer cell membrane of infected cells, thereby initiating a potent and an improved immune response.

Calreticulin (CRT) seems to be a multifunctional protein and has been described to be involved in transcription regulation of hormone-responsive DNA-elements and in the maturation of MHC class I proteins; it has also been described to bind and inactivate $Ca^{2+}$ ions or misfolded proteins in the endoplasmic reticulum, and primarily be located in the storage compartments of the endoplasmic reticulum (ER). CRT represents the most abundant protein of the ER lumen, but a fraction of the protein can translocate from the ER lumen to the surface of the cell in case of cell death; more specifically, it has been suggested that CRT acts as an "eat-me" signal on the cell surface (Gardai et al., 2005), mediating the engulfment by CD91-positive cells (mostly macrophages and dendritic cells (DCs)).

The novel Vaccinia virus strain is described to be replication competent in mammalian cells. It is believed—without being bound by this theory—that this characteristic depends inter alia on the presence and functional activity of the K1L gene in the viral backbone. In particular, it has been shown that the novel strain replicates well in mammalian and particularly in human and mouse cell lines, for example in cancer cells such as HeLa cells, 143B cells, CT26 cells, LLC1 cells or MCF-7 cells. In comparison to these results it should be noted that MVA is known not to replicate in these cells or in other cells of mammalian origin.

Furthermore, the novel Vaccinia virus strain shares several house-keeping genes with all and/or at least some of the other Vaccinia virus strains. It is, however, quite distinct in its immunological profile and is named IOVA (Immune-Oncolytic Vaccinia) in the context of the present application.

Many genes of the Vaccinia virus genome have been described to be immune evasion genes (Smith et al., 2013), which form and determine the immunological profile of the different virus strains. Over the years, studies have been conducted to identify the potential mechanism of action of such immune evasion genes. According to the results obtained these immune evasion genes express—inter alia—soluble receptors for cytokines, which compete with the natural receptors and, reduce the efficacy of a cytokine-induced immune response. Other genes block the intracellular pathways for activating different immune-activating genes and, thus, also interfere and reduce a virus specific immune response.

For a short summary, Table 1 lists the presently identified immune evasion genes of Vaccinia virus and their presence or absence in different Vaccinia strains. It also indicates a potential function or mechanism of action of the corresponding gene product.

TABLE 1

Known Vaccinia immune modulators compared to IOVA sequence

| ORF | GENE PRODUCT | IOVA | CVA | MVA | COP | WR |
|---|---|---|---|---|---|---|
| C12L | Interleukin-18-binding protein | + | + | − | + | + |
| C10L | Binds DNA--PK | − | − | − | + | + |
| C9L | Ant-like protein | − | − | − | + | + |
| C8L* | Interleukin-18 binding protien | + | + | + | − | + |
| C6L | IRF3 binding | + | + | + | + | + |
| C5L | Kelch-like protein | + | + | − | + | + |
| C4L | NF-κB inhibitor | − | − | − | + | + |
| C3L | Complement control protein | + | + | − | + | + |
| C2L | Kelch-like protein, modulator of inflammation | − | − | − | + | + |
| N1L | Inhibitor of TNF-R and TLR signaling | − | + | − | + | + |
| N2L | IRF3 inhibitor | − | + | − | + | + |
| M1L | Apoptosis inhibitor | − | − | − | + | + |
| K1L | NF-κB inhibitor | + | + | − | + | + |
| K2L | Serine protease inhibitor; SPI-3 | + | + | + | + | + |
| K3L | eIF2α-like protein | + | + | + | + | + |
| K7R | NF-κB/IRF3 inhibitor | + | + | + | + | + |
| F1L | Anti-apoptotic, inflammasome inhibitor | + | + | + | + | + |
| F3L | Kelch-like protein | + | + | − | + | + |
| E3L | Double-stranded RNA-binding protein | + | + | + | + | + |
| H1L | Dephosphorylates STAT1 and STAT2 (VH1) | + | + | + | + | + |
| D9/D10 | Cleavage of 5-methylated caps on mRNAs | + | + | + | + | + |
| A35R | Inhibitor of MHC class II | + | + | + | + | + |
| A38L | CD47-like protein | + | + | + | + | + |
| A40R | C-type lectin-like protein | + | + | + | + | + |
| A41L | Secreted chemokine-binding protein | + | + | + | + | + |
| A42R | Profilin-1-like | + | + | − | + | + |
| A44L | 3 β-hydroxysteroid dehydrogenase | + | + | + | + | + |
| A46R | NF-κB/IRF3 inhibitor | + | + | + | − | + |
| A49R | NF-κB inhibitor | + | + | + | + | + |
| A52R | Toll/IL1-receptor inhibitor targeting IRAK2/TRAF6 | − | + | − | + | + |
| A53R | Soluble TNF receptor (CrmC) | − | + | − | − | − |
| A55R | Intracellular kelch protein immunomodulator | − | − | − | + | + |
| A56R | Haemagglutinin/Blocker of NK cell lysis | − | + | + | + | + |
| B7R | Chemokine-binding domain protein SCP-3 | + | + | − | + | + |
| B8R | Secreted Interferon-γ binding protein | + | + | − | + | + |
| B13R/B14R | Inhibitor of caspases (SPI-2, CrmA) | − | − | − | − | + |
| B15R | Secreted IL-1β binding protein | + | + | − | + | + |
| B16R | Interleukin-1 beta receptor | + | + | + | − | + |

TABLE 1-continued

Known Vaccinia immune modulators compared to IOVA sequence

| ORF | GENE PRODUCT | IOVA | CVA | MVA | COP | WR |
|---|---|---|---|---|---|---|
| B19R | Soluble and cell surface interferon-α/β receptor | + | + | − | + | + |
| B21R* | Chemokine-binding domain protein SCP-1 | − | − | − | − | + |

ORF: Nomenclature of Vaccinia COP strain.
*Nomenclature in CPXV-GRI.
+: Full and functional;
−: Completely or partially deleted (non-functional).

The nomenclature of the open reading frames (ORF) used in Table 1 refers to the naming system established for the Vaccinia Virus Copenhagen (COP) strain (Goebel et al. 1990) and is identified by letters of the alphabet assigned to DNA fragments of the viral genome generated by the restriction endonuclease HindIII descending in size. Exceptions are the ORF C8L and B21R with letters referring to DNA fragments in the cowpox virus CPXV-GRI genome, due to their absence in the Vaccinia Virus COP strain. The different ORF in such HindIII fragments are identified by numbers. The letter at the end indicates the direction of transcription: R for right, L for left.

In addition, Table 1 provides a comparison regarding functionality of the so far identified immune evasion genes with the well-characterised Vaccinia virus strains COP, WR, MVA, as well as the MVA ancestor strain CVA. It is indicated in Table 1, whether the different genes are functional (indicated by "+"), partially/fully deleted and functionally inactive (indicated by "−") in the different virus genomes.

The novel Vaccinia virus strain, as described herein and in the following identified as IOVA, has an immunological profile of its own. It shares some of the functionally expressed genes with CVA or WR and also shares some of the functionally inactive genes with MVA. This has been confirmed by the inventors also on a sequence level, comparing the full-length sequence of one isolate of the novel Vaccinia virus IOVA with the published sequences of WR, COP, CVA, and MVA.

The inventors also developed a PCR assay for easy identification of the novel IOVA strain. For this, a fragment of the DNA of any Vaccinia virus to be tested can be amplified with PCR oligonucleotides (primers) specifically binding in the region or sequence of the C2L ORF (Open Reading Frame) on the one hand and in the region or sequence of the N2L ORF. A PCR performed by standard parameters will produce for most Vaccinia viruses an amplification fragment comprising the sequence of the ORF C2L-C1L-N1L-N2L. These PCR products are double-stranded DNA fragments and as such are then subject to an enzymatic treatment with the restriction endonuclease BstXI. As a result, the specific DNA products obtained in e.g. Vaccinia strains WR, COP and CVA would not be cleaved and present a single band of around 3280 bp (molecular weight) upon agarose gel electrophoresis. In contrast, the specific IOVA DNA product will be cleaved by BstXI and will present two bands in the agarose gel with molecular weights of about 2360 and 920 bp. The explanation is that the novel IOVA virus carries a highly specific mutation in the N1L ORF leading to a functional inactive N1L and a new BstXI restriction site. In the case of MVA, the C2L gene sequence is deleted in the MVA genome, accordingly there will be no amplification of a DNA product by this specific PCR.

As can be seen in Table 1 and in the data presented in this application, IOVA—itself as well as all derivatives thereof—although it shares many genes and/or functional deletions with CVA, WR and MVA, is unique regarding not only its safety features but also its immunological profile.

This immunological profile—being the essential core of this invention—is correlated inter alia with the presentation of calreticulin on the outer membrane of a virus-infected cell.

Thus, the immunological profile of the novel strain is described to elicit—inter alia—a measurable calreticulin presentation on the outer membrane of a virus-infected cell. It is believed—without being bound by this theory—that this characteristic depends on functional inactivity, partial or full deletion of at least one of the immune evasion genes selected from the group consisting of the B21R*, C10L, C9L, C4L, C2L, N1L, N2L, M1L, A26R, A51R, A52R, A55R, A56R, and B13R/B14R (Vaccinia virus Cop strain nomenclature except*, which correspond to CPXV-GRI nomenclature) in the viral backbone.

As a consequence of these functionally inactive, partially or fully deleted genes, the newly generated virus has not only lost some of its capability to escape the immune response of the host, but additionally a shift in immune-evasion strategies has been introduced.

TABLE 2

Distinction between IOVA and WR

| ORF | GENE PRODUCT | IOVA | WR |
|---|---|---|---|
| C10L | Binds DNA-PK | − | + |
| C9L | Ant-like protein | − | + |
| C4L | NF-κB inhibitor | − | + |
| C2L | Kelch-like protein, modulator of inflammation | − | + |
| N1L | Inhibitor of TNF-R and TLR signaling | − | + |
| N2L | IRF3 inhibitor | − | + |
| M1L | Apoptosis inhibitor | − | + |
| A52R | Toll/IL1-receptor inhibitor targeting IRAK2/TRAF6 | − | + |
| A55R | Intracellular kelch protein immunomodulator | − | + |
| A56R | Haemagglutinin/Blocker of NK cell lysis | − | + |
| B13R/B14R | Inhibitor of caspases (SPI-2, CrmA) | − | + |
| B21R* | Chemokine-binding domain protein SCP-1 | − | + |

ORF: Nomenclature according to Vaccinia virus - COP strain.
+: Complete and functional;
−: Completely or partially deleted or functional inactivated.

Particularly interesting in this context is the effect that the calreticulin protein, which normally is strictly internal and located in the endoplasmic reticulum, but can—when translocated to the cell surface of cancer cells after the infection with the novel Vaccinia virus strain—initiate and intensify a specific immune reaction towards the virus-infected cells. Calreticulin is a Danger Associated Molecular Pattern (DAMPs) described to act as an "eat-me" signal when presented on the outer membrane and can been used as a marker of an immunogenic cell death. In comparison to Vaccinia virus WR the newly generated Vaccinia virus strain, IOVA, lyses or kills cancer cells at a much lower dose and, thus, much more efficient (FIG. 3A).

It was shown by the inventors that in both human and mouse cell lines, WR was only able to kill 70-80% of cultured tumour cells; around 20-30% of the cells escaped the virus-mediated destruction and remained metabolically active even with highly increased multiplicity of infection.

On the contrary, a derivative of the novel IOVA virus destroyed at least and even more than 95% of the cells in all cell lines tested; very astonishing, in the human cell line HeLa, the novel IOVA derivative demonstrated a highly improved cytotoxicity, being at least 40 times more efficient than Vaccinia virus WR, although with regard to growth capacity of IOVA in HeLa it was very similar to that of Vaccinia virus WR. This more complete efficiency to kill virus-infected cells reduces particularly the risk of tumour remission and, thus, is highly advantageous.

Accordingly, it is not only highly advantageous to use the novel Vaccinia virus strain for the infection of cell cycle activated cells and/or tumour cells, and in this context particularly for the use as oncolytic virus or for use in the treatment of cancer, but also for vaccination purposes and more general immune stimulation purposes, thus for a use in medicine in general.

Additionally, according to a further embodiment, the novel Vaccinia virus strain IOVA comprises functionally inactive A56R gene. The lack of expression of the product of this gene correlates with the capacity of the virus to fuse infected cells with neighbouring cells and, i.e. to form syncytia upon infection of mammalian cells and tumour cells.

Syncytia formation has been described in many viral infections and, in most of these infections, its formation is as consequence of the membrane destabilization caused by a cytopathic effect; however, some other viruses encode proteins that promote this syncytia formation as a mechanism to spread the infection without being a target to neutralising antibodies. Interestingly, the A56R gene product is expressed by Vaccinia virus WR in order to inhibit such syncytia formation (FIG. 1).

The finding that the novel Vaccinia virus strain IOVA causes syncytia formation in cancer cells is considered as a potentially interesting phenotype for oncolytic viruses as syncytial cell death has been described to be highly immunogenic: fusion of tumour cells triggers the release of exosome-like vesicles associated with an effective release of tumour antigens, which can efficiently be uptaken by dendritic cells and thus improve a highly specific immune reaction.

Additionally, according to a further embodiment, the novel Vaccinia virus strain IOVA comprises functionally inactive A26R and A56R genes. The lack of expression of the product of these genes correlates with an even improved formation of syncytia upon infection of mammalian cells and tumour cells and thus, also correlates with the capacity of the virus to fuse infected cells with neighbouring cells.

To investigate syncytia formation as a possible mediator of IOVA virus-specific anti-tumour efficacy and the effect of the deletion of A56R alone or in combination with the deletion of A26R in such fusion, a single A56+ IOVA virus variant was engineered by replacing the mutated A56R gene and creating the IOVA/A56+ (FIGS. 1 and 6). When the A56R gene expression is restored, the IOVA/A56+ virus conserves a certain capacity to fuse tumour cells, although the number of fused cells is reduced compared to the IOVA/A26−/A56− virus (FIG. 6); this indicates that both genes may interact to fully inhibit the fusion of infected cells.

Syncytia formation is known to have a negative impact on the productive replication of other candidate oncolytic viruses, e.g. derived from measles virus or adenovirus. Surprisingly, syncytia formation in the context of IOVA viruses has been demonstrated to have a minimal impact on the replicative capacity, and very similar viral yields were obtained from cells infected with IOVA/A56− and IOVA/A56+ (FIG. 2).

Surprisingly, the formation of syncytia had a remarkable positive impact on cancer cell cytotoxicity according to the present invention: in all cell lines tested the syncytia-forming virus performed a more effective killing of cancer cells, especially in 143B and MCF-7 cancer cell lines, where IOVA/A56+ behaved similarly to Vaccinia virus WR with reduced killing of the cultured cancer cells (FIG. 3) Thus, syncytia formation mediated by IOVA/A56− and also IOVA/A56−/A26− can contribute to enhanced destruction of cancer cells.

A large-plaque phenotype was observed after the infection of cancer cells. Both IOVA/A56− and IOVA/A56+ viruses present an increased capacity to kill and to spread in cancer cells as shown by increased diameter of the plaques generated after the infection of a single cancer cell (FIG. 7).

In terms of inducing immunogenic cell death, syncytia formation is also independent from the induction of CRT translocation, and also from the later described additional secretion of further DAMPs such as HMGB1 and ATP, which was very similar for both A56− and A56+ viruses (FIG. 4*a*-*c*).

Interestingly, in the context of the present invention, it was shown that the phenotype of syncytia formation, which on its own already has an enhancing cytopathic effect in cancer cells, in addition to the independent exposure of calreticulin on the outer membrane of the infected cell, increased even more the antitumor effectiveness of the immune-modulated Vaccina virus strain IOVA as herein described.

Accordingly, the novel Vaccinia virus strain may contain additionally functionally inactive A56R and/or A26R genes and thus, cause syncytia formation and induce the fusion of tumour cells. In combination with the enhanced presentation of calreticulin on the membrane of the infected cell this leads to an even greater lytic and, thus, anti-tumour activity and results in consequence in enhanced destruction of cancer cells, tumour masses and eventually the generation of stronger immune responses against tumours.

In order to increase the safety of the novel IOVA virus, derivatives thereof and/or viral vectors thereof, additional modifications have been or may be introduced to restrict the replication to a specific cell range only.

Therefore, according to another embodiment the novel Vaccinia virus strain, IOVA, is modified to have a host range or, in other words, cell-range restricted replication competence in replicating cells and/or cancer cell.

In this context the term "replicating cell" comprises cells that have an activated cell-cycle and replicates at a high index. The cells falling under this definition comprise cells that are continuously replicating such as cancer cells, but also cells belonging to e.g. the activated immune system and optionally having the potential to infiltrate tumours.

Further the term "cancer cell" as used hereinafter comprises cells that divide inexorably and uncontrolled and have the capability to supersede or dispossess normal tissue by e.g. forming solid tumour mass or by flooding the blood and/or other body cavities with abnormal cells. Furthermore, the term "cancer cell" optionally refers also to cells that express and can be identified by their expression of known tumour marker gene products.

To improve the cell range specificity of the novel Vaccinia virus strain, it was shown that by inactivating one or more of the so-called house-keeping genes selected from the group consisting of F4L, J2R and C11R, a cell-range restricted replication competence can be obtained. For example, a virus with an inactivated or mutated J2R gene will not express the viral thymidine kinase and, thus, its effective replication will be limited to cells with a continuously activated cell-cycle or alternatively, to tumour cells. According to the present invention, such inactivation has been exemplarily performed by the insertion of an alternative expression cassette (expressing a tracer colour) onto the location of the TK gene, which in Vaccinia nomenclature is referred to as J2R.

Similarly, also the functional inactivation, deletion or mutation of the C11R, the F4L alone or in combination with each other or J2R, will limit the replication competence of the Vaccinia virus strain, according to the present invention, to cell-cycle activated and/or tumour cells. Thus, such addition of mutations or deletions to the viral genome in order to functionally inactivate one or more gene of the group consisting of F4L, J2R and C11R having the above-described consequence of a host range restriction, clearly improves the safety features for the novel virus strain.

Therefore, the cell range restricted Vaccinia virus strain, IOVA, is particularly advantageous for use in medicine because of its improved safety features.

It has been further shown by the inventors that the novel Vaccinia virus strain of the present invention is—compared to Vaccinia virus WR—surprisingly capable of inducing an immunogenic cell death upon infection.

In this context the term "immunogenic cell death" is to be understood as a form of cell death that is able to initiate and activate an immune response against the dying cell and is characterized by the release or exposure of damage-associated molecular pattern (DAMP) molecules, which can arouse an immune response against neo-antigens, both microbial and oncogenic (Galluzzi et al., 2017). Among a long list of DAMPs released or exposed by dying cells that may mediate an immune response to tumour cells, the exposure of calreticulin on the cell surface of cells, and independently the release of high-mobility group box 1 protein (HMGB1) or ATP into the extracellular space have been described.

Immunogenic cell death can further be described as a form of cell death that expose or release different DAMPs in order to activate dendritic cells (DCs) and consequent activation of specific T cells against antigens present in the dying cell. It is not triggered from the outside, as e.g. apoptosis, which is for example defined as non-immunogenic and even tolerogenic cell death and cannot be defined by the same DAMPs.

With the background knowledge of such markers, it was possible for the inventors to actually describe and classify the type of cell death caused by the viruses. And consequently, it was clearly demonstrated that in comparison to Vaccinia virus WR, the novel Vaccinia virus strain, IOVA, did cause not only an increased lytic and cell killing effect upon infection, but it was also possible to show by measuring some of the DAMPs, namely HMGB1 and ATP, and by measuring the amount of CRT presented on the outer cell membrane that the infected cells died due to an immunogenic cell death.

This proves impressively that the novel Vaccinia virus strain, which replicates in mammalian cells and specifically in tumour cells or cell-cycle activated cells, is highly useful not only as vaccine or adjuvant for vaccination purposes, but also in the context of further immunotherapeutic or immuno-oncological treatments, particularly as oncolytic virus for its use in the treatment of cancer.

In summary, the novel Vaccinia virus strain IOVA as well as its derivatives, vectors and recombinants have the ability to replicate in mammalian cancer lines and can be described as being lytic or, in case of cancer cells, oncolytic, as they elicit—compared with the gold standard Vaccinia virus WR—an increased capacity to destroy cell-cycle activated cells and/or tumour cells.

Importantly, IOVAs and derivatives or recombinants thereof are particularly suitable to induce an immunogenic cell death upon infection of cells and thereby are highly promising to be used in immunotherapeutic approaches. They are particularly suitable as novel platform viruses for a safe and efficient immunotherapeutic or immuno-oncologic treatment.

According to a further embodiment, the present application also provides an isolated IOVA virus characterised by its nucleic acid sequence. The sequence information of the isolated IOVA may comprise base pair modifications, which—however—do not affect the immunological profile of IOVA. Thus, an IOVA virus can be identified by sequence analysis and the presence of at least one or more functionally inactivate or deleted ORF selected from the group consisting of the J2R, C11R, F4L, B21R*, C10L, C9L, C4L, C2L, N1L, N2L, M1L, A26R, A51R, A52R, A55R, A56R, and B13R/B14R.

According to one further embodiment IOVA and its derivatives can be identified by the presence of a unique nucleotide sequence stretch of the C2L-C1L-N1L-N2L (SEQ ID NO.: 1), which introduces in the N1L ORF a newly generated BstXI restriction enzyme site. In this sequence, C2L incorporates a deletion of 51 nucleotides distributed in 3 microdeletions; N1L incorporates a 2 nucleotides deletion that incorporates an early termination codon; and N2L incorporates a 15 nucleotides deletion that codifies for a shorter N2L version. Thus, the sequences shown in SEQ ID No.1 is a unique sequence of IOVA and represents the unique stretch of for the C2L-C1L-N1L-N2L region of IOVA, incorporating microdeletions in some of the ORFs, but not complete deletions of such genes and no microdeletion of the C1L ORF, which is functional.

Additionally, the isolated IOVA—according to one embodiment—is considered to be a platform technology, which allows the generation of related derivatives or recombinants, identified by the PCR analysis as mentioned above or a direct sequence comparison of at least one or more of the viral housekeeping or the functional inactive immune evasion genes selected from the group of ORFs consisting of the K1L, A56R, A26R, J2R, C11R, F4L, B21R*, C10L, C9L, C4L, C2L, N1L, N2L, M1L, A51R, A52R, A55R and B13R/B14R.

According to a further embodiment the present application also provides a viral vector derived from IOVA. This viral vector comprises the same set of functionally active and functionally inactive genes as IOVA. The term "viral vector" in the context of this application also includes two or more vector molecules each comprising or carrying parts or ranges of the set of functionally active and functionally inactive genes of IOVA working in concert to transfect a cell enabling IOVA to be produced from such cell.

IOVA itself, the isolated virus, the nucleic acid sequence of IOVA and a viral vector(s) comprising the IOVA specific nucleic acid sequence are considered a platform technology.

Said IOVA platform comprises also derivatives of IOVA, which can be identified by PCR and a restriction enzyme digest with the BstXI enzyme and which still employ the same functional features and characteristics as IOVA, particularly the replication competence in mammalian cellcycle-activated cells, the calreticulin translocation to the outer membrane and/or independently the induction of syncytia formation in infected cells.

Said IOVA platform further comprises recombinants of IOVA. The backbone of IOVA contains several well-described Vaccinia virus insertion sites for transgenic insertions into its genome. Due to its close relation to Vaccinia virus the skilled practitioner knows and is capable of using one or several locations for the insertion of transgenes, such as e.g. genes encoding tumour antigens, tumour associated antigens, disease associated antigens and/or pathogen derived antigens.

According to a further embodiment, the invention thus provides a recombinant or transgenic IOVA or a derivative or viral vector thereof. As in every platform technology, the introduction of additional genes or genetic information in well-described insertion sites does not affect the main characteristics of the claimed platform members, these independently being (i) the induction of a fusion or syncytia formation of infected cells, (ii) the induction of a prominent release or exposure of DAMPs, particularly of calreticulin and/or (iii) the induction of an immunogenic cell death of the infected cell, which may contribute to an even greater immunological effect or in case of the infection of tumour cells a more effective anti-tumour activity through enhanced destruction of tumour cells.

It is believed—without being bound by the theory—that the more effective anti-tumour activity is particularly due to a stronger immune response against such infected cells, which may be triggered by presentation of calreticulin and/or an increased release of other DAMPs, such as HMGB1 or ATP. Released HMGB1 can bind to TLR4 and RAGE and trigger proinflammatory responses, while released ATP seems to act also as a "find-me" signal for immune cells.

In summary, the novel Vaccinia virus strain IOVA as well as its derivatives, vectors and recombinants have the ability to replicate in mammalian cancer lines and can be described as being lytic or, in case of cancer cells, oncolytic, as they elicit—compared with the gold standard Vaccinia virus WR—an increased capacity to destroy cell-cycle activated cells and/or tumour cells.

IOVA or its derivatives, due to its unique immunological profile and its safety features, which are comparable or even better than in already well-established Vaccinia virus strains, can thus be used in medicine, particularly in oncological approaches or as an oncolytic or as a vaccine against cancer or other pathogens.

Importantly, IOVA viruses and derivatives or recombinants thereof are particularly suitable to induce an immunogenic cell death upon infection of cells and are thereby highly recommended to be used in immunotherapeutic approaches. They are particularly suitable as novel virus platform for a safe and efficient immunotherapeutic or immuno-oncologic treatment.

SHORT DESCRIPTION OF THE FIGURES

FIG. 1. Syncytia formation in cancer cells after infection with IOVA viruses. Fluorescent photomicrographs (40×) are shown after infection of (a) human or (b) mouse cancer cell lines (24 hours post-infection). HeLa and CT26 cells were infected with an MOI of 0.5. 143B, MCF-7, and LLC1 were infected with an MOI of 5. mCherry is expressed from all the viruses under the P11 promoter. Massive fusion of cells (syncytium) can be observed when cells were infected with IOVA/A56−.

FIG. 2. Viral production of IOVA viruses in human and mouse tumour cells. (a) Human and (b) mouse tumour cell lines were infected with WR/TK−, IOVA/A56−, or IOVA/A56+ at an MOI of 5, and progeny was measured by plaque-assay at different time points. Viral yield was evaluated in quadruplicate for each cell line, by carrying two independent experiments. Means+SD are plotted. *, significant $p<0.05$ compared with WR/TK−. #, significant $p<0.05$ compared with IOVA/A56+.

FIG. 3. IOVA viruses present increased cytotoxicity to tumour cells. Cancer cells were infected with WR/TK−, IOVA/A56−, or IOVA/A56+ at doses ranging from 100 to 0.0005 PFU/cell. At day 3 after infection, viability of cells was determined. Both human (a) and mouse (b) cancer cells were tested. Four different replicates were quantified for each cell line and mean±SD of each MOI is depicted.

FIG. 4. Induction of Immunogenic Cell Death by IOVA viruses. (a) Analysis of Calreticulin expression on the surface of infected cells. Indicated tumour cell lines were infected with WR/TK−, IOVA/A56−, or IOVA/A56+ with an MOI of 5, and 24 hours after infection Calreticulin+ cell populations were determined by flow cytometry. Uninfected cells (Mock) and Staurosporin 1 μM were used as negative and positive controls, respectively. (a) Percentage of Calreticulin+ cells. Values of individual replicates and means±SEM of the different treatments are plotted. (b-c) Concentration of HMGB1 (b) and ATP (c) in cell supernatant after infection with IOVA viruses. ELISA assays and ENLITEN ATP assay system were utilized, respectively, to determine such concentrations at 24 hours after infection (MOI of 5) of indicated tumour cell lines. Data were obtained in quadruplicate and are plotted as fold change versus WR/TK−+SD. *, significant $p<0.05$ compared with WR/TK−. #, significant $p<0.05$ compared with Mock.

FIG. 5. PCR Assay for Virus identification. FIG. 5a: Sequence of the PCR product employed in the PCR Assay. FIG. 5b: Results of the PCR assay clearly identify the sequence of IOVA strain as the assay generates a unique pattern of two bands (2320 and 920 bp) for IOVA, in contrast to all the other Vaccinia virus strains, which present a single band of 3300 bp for WR, COP and CVA. MVA strain generates no amplified product due to a C2L deletion.

FIG. 6. Number of nuclei in syncytia after infection with IOVA viruses. Human tumour cell lines were infected with WR/TK−, IOVA/A56−/A26−, or IOVA/A56+/A26− at an MOI of 5. At 16 hours post-infection, cultures were dyed with Hoechst 33342 and the number of nuclei in one syncytium were counted under the microscope. Values of individual replicates and means±SEM are plotted. ***, significant $p<0.0001$ compared with WR/TK−.

FIG. 7. Size of the plaques in cancer cells. Cancer cell monolayers were infected with indicated viruses for 1 hour at an MOI of 0.0001 and cultivated for 4 days covered with a 1:1 mixture of culture media and 1% carboxymethylcellulose. After fixation and staining with crystal violet, the diameter of the plaques was determined. Values of individual replicates and means±SEM are plotted. *, significant $p<0.05$ compared with WR/TK−. #, significant $p<0.05$ compared with IOVA/A56−.

EXAMPLES

Example 1: Deletions in IOVA Genome

A novel Immune-Oncolytic Vaccinia virus (IOVA) strain is generated incorporating a deletion in the thymidine kinase (TK, J2R) gene in order to confer selective replication in cancer cells. Additionally, the mCherry gene has been cloned into the TK site under the control of the Vaccinia virus-specific promoter P11 in order to monitor virus replication.

In addition, the newly generated IOVA contains several deletions or functional inactivations among genes considered to be immune modulators and selected from the ORF of B21R*, C10L, C9L, C4L, C2L, N1L, N2L, M1L, A26R, A51R, A52R, A55R, A56R, and B13R/B14R. The functions of the proteins coded for these genes are summarized in Table 1 above.

The IOVA genome is further characterised by the inclusion of a mutated version of the A26R and/or the A56R gene. The presence of A26 protein in the virion prevents direct virus-cell fusion mechanism and its deletion has been associated with induction of syncytia. A56R encodes a viral regulatory protein with haemagglutination activity, and its inactivation in Vaccinia virus is believed to result in viruses with a fusogenic phenotype. All gene deletions or partial deletions as well as all functional inactivation or gene insertions have been confirmed by sequencing.

Example 2: Syncytia Formation Induced by IOVA

In order to evaluate the pros and cons of syncytia formation for tumour destruction, the inventors restored by homologous recombination the wild-type Vaccinia virus A56R gene sequence in the novel IOVA genome. The resulting virus was named IOVA/A56+, in comparison to the IOVA with the truncated A56R version, which was named IOVA/A56−.

Upon infection, it was observed (FIG. 1), that cells infected with the IOVA/A56− virus fuse with neighboring cells, and a formation of huge syncytia could be clearly observed in both human and mouse tumour cell lines traced by the mCherry expression. As hypothesized, the expression of wild-type A56 in IOVA/A56+ restored a phenotype very similar to Vaccinia virus WR strain and did not lead to syncytia formation.

Additionally, it was observed that The expression of wild-type A56 in IOVA/A56−/A26− may be described also as only partially blocking the formation of syncytia, as still a fusion of up to 10 cells could be observed after infection with IOVA/A56+/A26− (FIG. 6).

Example 3: Replication Competence of IOVA

We tested the replication competence of IOVA in comparison with the standard strain Vaccinia virus WR in a wide panel of human and mouse cancer cell lines.

For monitoring the replication of the newly generated IOVA, the replication capacity of two IOVA virus isolates (A56− and A56+) and WR/TK− as a control was tested in several human and mouse cancer cell lines.

For this, human and mouse tumour cell lines were infected with WR/TK−, IOVA/A56−, or IOVA/A56+ at an MOI of 5, and progeny was measured by plaque-assay at different time points. Viral yield was evaluated in quadruplicate for each cell line, by carrying two independent experiments (previously described in: Rojas J J et al., Cell Rep. 2016).

As shown in FIG. 2, both IOVA viruses (A56− and A56+) performed a growth curve very similar to control strain WR/TK− in most cell lines tested, with only a slight reduction of the yield at early time points for the syncytia-forming IOVA.

Example 4: Cytotoxicity of IOVA

We examined the cytotoxic effect of an IOVA infection in comparison with the standard strain Vaccinia virus WR in a wide panel of human and mouse cancer cell lines.

For this, various cancer cell lines were infected with WR/TK−, IOVA/A56−, or IOVA/A56+ at doses ranging from 100 to 0.0005 PFU/cell. At day 3 after infection, viability of cells was determined. Both human and mouse cancer cells were tested. Four different replicates were quantified for each cell line and mean±SD of each MOI is depicted.

Interestingly, infections with the IOVA viruses resulted in clearly enhanced levels of cytotoxicity in cancer cell compared to Vaccinia virus WR (FIG. 3). Vaccinia virus WR was able to kill around 70-80% of the cancer cells in culture, even when at the highest multiplicity of infection (MOI). On the contrary, IOVA/A56− virus was able to kill between 95-100% of the cultured tumour cells and reduced the EC50 (amount of virus necessary to kill 50% of the cells).

Surprisingly, IOVA/A56− decreased the amount of virus required to reduce 50% of cell culture viability of HeLa cells by more than 40 fold compared to Vaccinia virus WR (WR/TK−). IOVA/A56+ also presented a phenotype with enhanced cytotoxicity for cancer cell in vitro; the A56-restored virus killed HeLa, CT-26, and LLC1 cells at similar rates as IOVA/A56−. Yet in 143B and MCF-7 cells the cytotoxicity was very similar to that obtained with WR/TK− infection, suggesting that virus-mediated big syncytia formation may contribute to enhanced destruction of tumours.

Example 5: Large Plaque Phenotype of IOVA Viruses in Cancer Cells

An increased size of the plaques in cancer cells has been associated to a better spread of the virus throughout the tumour and to a higher antitumor activity. For testing the plaque size of IOVA viruses, a panel of cancer cell lines were infected at a MOI of 0.0001 and, after 1 hour of infection, the infected cells were cultured with a carboxymethylcellulose overlay. For 4 after the infection, the cultures were fixed and dyed with crystal violet and the diameter of the plaques were determined.

As shown in FIG. 7, both IOVA/A56− and IOVA/A56+ induced larger plaques in all cancer cell lines tested compared to WR/TK− virus control. In HeLa cells, plaques after infection with IOVA viruses were as a mean 40% larger compared to WR/TK−. Impressively, very large plaques could be observed after infection of 143B and MCF-7 with IOVA viruses, with plaques 2 times the diameter of plaques generated by WR/TK− in the case of 143B cells and plaques 2.6 time larger in the case of MCF-7.

With regard to plaque size, the generation of big syncytia by IOVA/A56− do not have a significant influence except in the case of MCF-7 breast cancer cell line, were IOVA/A56+ virus generated plaques 1.4 times smaller compared to IOVA/A56−.

Example 6: IOVA Viruses Induce Presentation of Calreticulin on Cellular Membrane and Immunogenic Cell Death of Cancer Cells In order to test whether the IOVA viruses may be able to elicit and potentiate an immune response against cancer cells, the inventors initially analysed by flow cytometry the exposure of calreticulin (CRT) on the surface of human cancer cells after infection with IOVA/A56−, IOVA/A56+, or the control virus WR/TK−.

For this, cells were infected with an MOI of 5 and, 24 hours after virus infection, detached using a non-enzymatic cell dissociation solution. Calreticulin was detected by incubating the cells for 1 hour at 4° C. with a human anti-calreticulin-AlexaFluor405 antibody (Abcam, Ref N° ab210431). Uninfected cells and staurosporin (1 μM) were used as negative and positive controls, respectively.

Upon infection of HeLa cells, WR/TK− induced a surface-exposure of CRT on around 15% of the cells (FIG. 4a); on the contrary, surprisingly high levels of more than 80% of the cells expressed CRT on the surface upon infection with both IOVA viruses. Similarly, exposure of CRT increased from around 35% (with WR/TK−) to almost 90% (with IOVA viruses) in 143B cells, and from 3% to more than 72% in MCF-7 cells.

In order to further investigate the possible induction of a pronounced immunogenic cell death upon infection with IOVA viruses, the release of HMGB1 and ATP was determined using an ELISA assay and a luciferase-mediated ATP assay system, respectively.

In all cell lines tested and with both IOVA/A56− and IOVA/A56+, significantly higher concentrations of HMGB1 could be detected in the supernatant of infected cells compared with cells infected with WR/TK− (FIG. 4b), with an increase ranging from 1.23 times (143B cells, IOVA/A56−) to 1.68 times (MCF-7 cells, IOVA/A56+). ATP concentration on the supernatant of infected cells was also increased when infected with the IOVA viruses compared to the levels after infection with WR/TK− (FIG. 4c), with an increase ranging from 1.12 times (143B cells, IOVA/A56+) to 2.27 times (HeLa, IOVA/A56−).

These results indicated that IOVA virus, but not Vaccinia virus WR, induces an immunogenic cell death of infected human cancer cells. Thus, IOVA can be suggested as a particularly promising candidate virus that may represent a huge benefit in terms of anti-tumour activity in clinical trials.

Example 7: PCR Assay for the Identification of IOVA Viruses or their Derivatives In order to identify IOVA strain, the DNA of the virus is isolated by digesting the cell extract of infected cells with proteinase K, and by using a QIAamp genomic DNA kit (QIAGEN) following manufactured instructions. A unique sequence of IOVA covering the C2L-C1L-N1L-N2L fragment (FIG. 5a; SEQ ID No.1) is amplified by PCR using the following oligos: Forward 5'-ATGTTATCCTGGA-CATCGTAC-3' (SEQ ID No. 2) and Reverse 5'-TCATGACGTCCTCTGCAATGG-3' (SEQ ID No. 3). The PCR product using these two primers is 50 bp larger than the unique SEQ ID No.1; for stability reasons, 50 more bp were included in design of the PCR reaction. The PCR product (SEQ ID No.4) is purified by using a QIAquick PCR purification kit and is digested with BstXI restriction enzyme.

By using this assay, IOVA strain can be clearly identified as it generates a specific and unique pattern of two DNA bands (2361 and 923 bp) visualized by electrophoresis in 1% agarose, in contrast to all the other Vaccinia strains, which present a single band of 3384 bp. PCR of MVA genomic DNA generates no PCR product due to the absence of the C2L sequence (FIG. 5b).

REFERENCES

D. Kirn, T. Hermiston, F. McCormick, ONYX-015: clinical data are encouraging. Nature medicine 4, 1341 (December 1998).

C. J. Breitbach et al., Oncolytic vaccinia virus disrupts tumour-associated vasculature in humans. Cancer research 73, 1265 (Feb. 15, 2013).

S. H. Thorne et al., Targeting localized immune suppression within the tumour through repeat cycles of immune cell-oncolytic virus combination therapy. Molecular therapy: the journal of the American Society of Gene Therapy 18, 1698 (September 2010).

C. J. Breitbach et al., Intravenous delivery of a multi-mechanistic cancer-targeted oncolytic poxvirus in humans. Nature 477, 99 (Sep. 1, 2011).

J. Heo et al., Randomized dose-finding clinical trial of oncolytic immunotherapeutic vaccinia JX-594 in liver cancer. Nature medicine 19, 329 (March 2013).

H. J. Zeh et al., First-in-man study of western reserve strain oncolytic vaccinia virus: safety, systemic spread, and antitumour activity. Molecular therapy: the journal of the American Society of Gene Therapy 23, 202 (January 2015).

A. Volz, G. Sutter, Protective efficacy of Modified Vaccinia virus Ankara in preclinical studies. Vaccine 31, 4235 (Sep. 6, 2013).

H. Meyer, G. Sutter, A. Mayr, Mapping of deletions in the genome of the highly attenuated vaccinia virus MVA and their influence on virulence. The Journal of general virology 72 (Pt 5), 1031 (May 1991).

R. T. Zhang, S. D. Bines, C. Ruby, H. L. Kaufman, TroVax((R)) vaccine therapy for renal cell carcinoma. Immunotherapy 4, 27 (January 2012).

I. Marigo, L. Dolcetti, P. Serafini, P. Zanovello, V. Bronte, Tumour-induced tolerance and immune suppression by myeloid derived suppressor cells. Immunol Rev 222, 162 (April 2008).

S. J. Gardai et al., Cell-surface calreticulin initiates clearance of viable or apoptotic cells through trans-activation of LRP on the phagocyte. Cell 123, 321 (Oct. 21, 2005).

G. L. Smith et al., Vaccinia virus immune evasion: mechanisms, virulence and immunogenicity. The Journal of general virology 94, 2367 (November 2013).

Goebel et al. The complete DNA sequence of vaccinia virus. Virology 1990 November; 179(1): 247-66, 517-63.

L. Galluzzi, A. Buque, O. Kepp, L. Zitvogel, G. Kroemer, Immunogenic cell death in cancer and infectious disease. Nat Rev Immunol 17, 97 (February 2017).

Rojas J J et al., Manipulating TLR signaling increases the anti-tumour T cell response induced by viral cancer therapies. Cell Rep., 2016 Apr. 12; 15(2): 264-73.

The invention claimed is:

1. A genetically modified, immuno-modulating Vaccinia virus, wherein the virus is identified by the presence of SEQ ID No.: 1, has a functional active K1L, is replication competent in mammalian cells, and induces calreticulin transiocation to the membrane of an infected HeLa cell.

2. The Vaccinia virus according to claim 1, wherein the virus has, additionally, a functionally inactivated A56R.

3. The Vaccinia virus according to claim 1, wherein the virus has a functionally inactivated A26R.

4. The Vaccinia Virus according to claim 1, wherein the virus additionally comprises one or more functionally inactivated immune-evasion genes selected from the group of open reading frames consisting of B21R, C10L, C9L, C4L, M1L, A51R, A52R, A55R, and B13R/B14R.

5. The Vaccinia virus according to claim 1, wherein the virus comprises, additionally, at least one functionally inactivated, partially deleted or fully deleted gene selected from the group consisting of J2R, C11R, and F4L.

6. The Vaccinia virus according to claim 1, wherein the virus is replication-competent and lytic in cell-cycle-activated cells and/or tumour cells.

7. The Vaccinia virus according claim 1, wherein the virus, upon infection, causes the formation of syncytia.

8. A nucleic acid sequence or fragment thereof encoding the Vaccinia virus according to claim 1.

9. A viral vector comprising the nucleic acid sequence according to claim 8.

10. The Vaccinia virus according to claim 1, characterised by carrying one or more insertion sites with at least one insertion of one or more transgenes.

11. The recombinant Vaccinia virus according to claim 10, wherein the transgene is selected from the group comprising genes encoding tumour antigens, tumour associated antigens, disease associated antigens, and pathogen-derived antigens.

12. A method of treating a subject, the method comprising administering to the subject the Vaccinia virus according to claim 1.

13. A method of treating cancer in a subject, the method comprising administering to the subject the Vaccinia virus according claim 1.

14. A pharmaceutical composition comprising the Vaccinia virus according to claim 1 and a pharmaceutically acceptable carrier, diluent, or excipient.

* * * * *

SEQUENCE LISTING

<160> NUMBER OF SEQ ID NOS: 4

<210> SEQ ID NO 1
<211> LENGTH: 3234
<212> TYPE: DNA

<213> ORGANISM: Vaccinia virus
<220> FEATURE:
<223> OTHER INFORMATION: C2L-C1L-N1L-N2L with new BstXI site

<400> SEQUENCE: 1

```
ctattgtaga aattgttttt cacagttgct caaaaacgat ggcagtgact tatgagtttc     60
atctttagta aacatatcat aatattcgat attactagtt gacatatcga acaaattcca    120
agtatttgat tttggataat attcgtattt tgcatctgct ataattaaga tataatcacc    180
gcaagaacac acgaacatct ttcctacatg gttaaagtac atgtacaatt ctatccattt    240
gtcttcctta actatatatt tgtatagata attacgagtc tcgtgagtaa ttccagtaat    300
tacatagatg tcgccgtcgt actctacagc ataaactata ctatgatgtc taggcatggg    360
agactttttt atccaacgat tttagtgaa acattccaca tcgtttaata ctacatattt    420
ttcatacgtg gtataaactc cacccattac atatatatca tcgtttacga ataccgacgc    480
gcctgaatat ctaggagtaa ttaagtttgg aagtcttatc catttcgaag tgccgtgttt    540
caaatattct gccacacccg ttgaaataga aaattctaat cctcctatta catataactt    600
tccatcgtta acacaagtac taacttctga ttttaacgac gacatattag taaccgtttt    660
ccatttttc gtttcaagat ctacccgcga tacggaataa acatgtctat tgttaatcat    720
gccgccaata atgtatagac aattatgtaa aacatttgca ttatagaatt gtctatctgt    780
attaccgact atcgtccaat attctgttct aggagagtaa tgggttattg tggatatata    840
atcagagttt ttaatgacta ctatattatg ttttatacca tttcgtgtca ctggctttgt    900
agatttggat atagttaatc ccaacaatga tatagcattg cgcatagtat tagtcataaa    960
cttgggatgt aaaatgttga tgatatctac atcgtttgga tttttatgta tccactttaa   1020
taatatcata gctgtaacat cctcatgatt tacgttaacg tcttcgtggg ataagatagt   1080
tgtcagttca tcctttgata attttccaaa ttctggatcg gatgtcaccg cagtaatatt   1140
gttgattatt tctgacatcg acgcattata tagtttttta attccatatc ttttagaaaa   1200
gttaaacatc cttatacaat ttgtggaatt aatattatga atcatagttt ttacacatag   1260
atctactaca ggcggaacat caattattat ggcagcaact agtatcattt ctacattgtt   1320
tatggtgatg tttatcttct tccagcgcat atagtctaat agcgattcaa acgcgtgata   1380
gtttatacca ttcaatataa tcgcttcatc ctttagatgg tgatcctgaa tgcgtttaaa   1440
aaaattatac ggagacgccg taataatttc cttattcact tgtataattt ccccattgat   1500
agaaaatatc acgctttcca ttcttgaagt actataagta attatagtat aatgtaaagg   1560
tttatatatt caatattttt tataaaaaaa tcatttcgac attaattcct ttttaaattt   1620
ccgtctatca tctatagaaa catattctat gaatttataa aatgctttta cgtgtcctat   1680
cgtaggcgat agaaccgcta aaaagcctat cgaatttcta caaaagaatc tgttatatgg   1740
tatagggaga gtataaaaca ttaaatgtcc gtacttatta aagtattcag tagccaatcc   1800
taactctttc gaatacttat taatggctct tgttctgtac gaatctattt ttttgaacaa   1860
tggacctagt ggtatatctt gttctatgta tctaaaataa tgtctgacta gatccgttag   1920
tttaatatcc gcagtcatct tgtctagaat ggcaaatcta actgcgggtt taggctttag   1980
tttagtttct atatctacat ctatgtcttt atctaacacc aaaaatataa tagctaatat   2040
tttattacaa tcatccggat attcttctac gatctcacta actaatgttt ctttggttat   2100
actagtatag tcacgatcag acaaataaag aaaatcagat gatcgatgaa taatacattt   2160
aaattcatca tctgtaagat ttttgagatg tctcattaaa atattattag ggtcagtact   2220
```

-continued cattatcatt aggcagctat tacttatttt attatttttc accatataga tcaatcatta 2280
gatcatcaaa atatgtttca atcatccaag agtatggtga atgactcttc ccatctaatt 2340
tctgaacgtt caccaatgtc tctagccact ttggcactaa tagcgatcat tcgcttagcg 2400
tcttctatat tattaactgg ttgattcaat ctatctagca atggaccgtc ggacagcgtc 2460
attctcatgt tcttaatcaa tgtacataca tcgccgtcat ctaccaattc atccaacaac 2520
ataagctttt taaaatcatc attataatag gtttgatcgt tgtcatttct ccaaagaata 2580
tatctaataa gtagagtcct catgattagt taacaactat tttttatgtt aaatcaatta 2640
gtacaccgct atgtttaata cttattcata ttttagtttt taggattgag aatcaataca 2700
aaaattaatg catcattaat tttagaaata cttagtttcc acgtagtcaa tgaaacattt 2760
gaactcatcg tacaggacgt tctcgtacag gacgtaacta taaaccggtt tatatttgtt 2820
caagatagat acaaatccga taactttttt tacgaattct acgggatcca ctttaaaagt 2880
gtcataccgg gttcttttta ttttttttaaa cagattaatg gtgtgatgtt gattaggtct 2940
tttacgaatt tgatatagaa tagcgtttac atattctcca taatggtcaa tcgccatttg 3000
ttcgtatgtc ataaattctt taattatatg acactgtgta ttatttagtt catccttgtt 3060
catcattagg aatctatcca atatggcaat tatactagaa ctataggtgc gttgtataca 3120
catattgatg tgtctgttta tacaatccat gctactacct tcgggtaaaa ttgtagcatc 3180
atataccatt tctagtactt taggttcatt gttatccatt gcagaggacg tcat 3234

<210> SEQ ID NO 2
<211> LENGTH: 21
<212> TYPE: DNA
<213> ORGANISM: Artificial Sequence
<220> FEATURE:
<223> OTHER INFORMATION: Primer

<400> SEQUENCE: 2
atgttatcct ggacatcgta c 21

<210> SEQ ID NO 3
<211> LENGTH: 21
<212> TYPE: DNA
<213> ORGANISM: Artificial Sequence
<220> FEATURE:
<223> OTHER INFORMATION: Primer

<400> SEQUENCE: 3
tcatgacgtc ctctgcaatg g 21

<210> SEQ ID NO 4
<211> LENGTH: 3284
<212> TYPE: DNA
<213> ORGANISM: Vaccinia virus
<220> FEATURE:
<223> OTHER INFORMATION: PCR Product

<400> SEQUENCE: 4
atgttatcct ggacatcgta caaataataa aaagcccata tatgttcgct attgtagaaa 60
ttgtttttca cagttgctca aaaacgatgg cagtgactta tgagtttcat ctttagtaaa 120
catatcataa tattcgatat tactagttga catatcgaac aaattccaag tatttgattt 180
tggataatat tcgtattttg catctgctat aattaagata taatcaccgc aagaacacac 240
gaacatcttt cctacatggt taaagtacat gtacaattct atccatttgt cttccttaac 300

```
tatatatttg tatagataat tacgagtctc gtgagtaatt ccagtaatta catagatgtc      360
gccgtcgtac tctacagcat aaactatact atgatgtcta ggcatgggag acttttttat      420
ccaacgattt ttagtgaaac attccacatc gtttaatact acatattttt catacgtggt      480
ataaactcca cccattacat atatatcatc gtttacgaat accgacgcgc ctgaatatct      540
aggagtaatt aagtttggaa gtcttatcca tttcgaagtg ccgtgtttca aatattctgc      600
cacacccgtt gaaatagaaa attctaatcc tcctattaca tataactttc catcgttaac      660
acaagtacta acttctgatt ttaacgacga catattagta accgttttcc atttttttcgt     720 ttcaagatct acccgcgata cggaataaac atgtctattg ttaatcatgc cgccaataat      780
gtatagacaa ttatgtaaaa catttgcatt atagaattgt ctatctgtat taccgactat      840
cgtccaatat tctgttctag gagagtaatg ggttattgtg gatatataat cagagttttt      900
aatgactact atattatgtt ttataccatt tcgtgtcact ggctttgtag atttggatat      960
agttaatccc aacaatgata tagcattgcg catagtatta gtcataaact tgggatgtaa     1020
aatgttgatg atatctacat cgtttggatt tttatgtatc cactttaata atatcatagc     1080
tgtaacatcc tcatgattta cgttaacgtc ttcgtgggat aagatagttg tcagttcatc     1140
ctttgataat tttccaaatt ctggatcgga tgtcaccgca gtaatattgt tgattatttc     1200
tgacatcgac gcattatata gttttttaat tccatatctt ttagaaaagt taaacatcct     1260
tatacaattt gtggaattaa tattatgaat catagttttt acacatagat ctactacagg     1320
cggaacatca attattatgg cagcaactag tatcatttct acattgttta tggtgatgtt     1380
tatcttcttc cagcgcatat agtctaatag cgattcaaac gcgtgatagt ttataccatt     1440
caatataatc gcttcatcct ttagatggtg atcctgaatg cgtttaaaaa aattatacgg     1500
agacgccgta ataatttcct tattcacttg tataatttcc ccattgatag aaaatatcac     1560
gctttccatt cttgaagtac tataagtaat tatagtataa tgtaaaggtt tatatattca     1620 atattttta taaaaaaatc atttcgacat taattccttt ttaaatttcc gtctatcatc      1680
tatagaaaca tattctatga atttataaaa tgcttttacg tgtcctatcg taggcgatag     1740
aaccgctaaa aagcctatcg aatttctaca aaagaatctg ttatatggta tagggagagt     1800
ataaaacatt aaatgtccgt acttattaaa gtattcagta gccaatccta actctttcga     1860
atacttatta atggctcttg ttctgtacga atctattttt ttgaacaatg gacctagtgg     1920
tatatcttgt tctatgtatc taaaataatg tctgactaga tccgttagtt taatatccgc     1980
agtcatcttg tctagaatgg caaatctaac tgcgggttta ggctttagtt tagttttctat    2040 atctacatct atgtctttat ctaacaccaa aaatataata gctaatattt tattacaatc     2100
atccggatat tcttctacga tctcactaac taatgtttct ttggttatac tagtatagtc     2160
acgatcagac aaataaagaa aatcagatga tcgatgaata atacatttaa attcatcatc     2220
tgtaagattt ttgagatgtc tcattaaaat attattaggg tcagtactca ttatcattag     2280
gcagctatta cttattttat tatttttcac catatagatc aatcattaga tcatcaaaat     2340
atgtttcaat catccaagag tatggtgaat gactcttccc atctaatttc tgaacgttca     2400
ccaatgtctc tagccacttt ggcactaata gcgatcattc gcttagcgtc ttctatatta     2460
ttaactggtt gattcaatct atctagcaat ggaccgtcgg acagcgtcat tctcatgttc     2520
ttaatcaatg tacatacatc gccgtcatct accaattcat ccaacaacat aagcttttta     2580
aaatcatcat tataataggt ttgatcgttg tcatttctcc aaagaatata tctaataagt     2640
agagtcctca tgattagtta acaactattt tttatgttaa atcaattagt acaccgctat     2700
```

-continued

```
gtttaatact tattcatatt ttagttttta ggattgagaa tcaatacaaa aattaatgca   2760
tcattaattt tagaaatact tagtttccac gtagtcaatg aaacatttga actcatcgta   2820
caggacgttc tcgtacagga cgtaactata aaccggttta tatttgttca agatagatac   2880
aaatccgata actttttta cgaattctac gggatccact ttaaaagtgt cataccgggt   2940
tctttttatt tttttaaaca gattaatggt gtgatgttga ttaggtcttt tacgaatttg   3000
atatagaata gcgtttacat attctccata atggtcaatc gccatttgtt cgtatgtcat   3060
aaattcttta attatatgac actgtgtatt atttagttca tccttgttca tcattaggaa   3120
tctatccaat atggcaatta tactagaact ataggtgcgt tgtatacaca tattgatgtg   3180
tctgtttata caatccatgc tactaccttc gggtaaaatt gtagcatcat ataccatttc   3240
tagtacttta ggttcattgt tatccattgc agaggacgtc atga                     3284
```